(12) United States Patent
Gaige et al.

(10) Patent No.: US 11,414,699 B2
(45) Date of Patent: Aug. 16, 2022

(54) BARCODE-FREE SINGLE VESICLE MULTIPLEXED PROTEIN AND RNA ANALYSIS

(71) Applicant: Mantra Bio, Inc., San Francisco, CA (US)

(72) Inventors: Terry Alden Gaige, Alameda, CA (US); Chi-Chih (Ginny) Kang, Berkeley, CA (US); Catherine RoseMary Planey, San Francisco, CA (US); Dragan Sebisanovic, Foster City, CA (US)

(73) Assignee: MANTRA BIO, INC., San Francisco, CA (US)

( * ) Notice: Subject to any disclaimer, the term of this patent is extended or adjusted under 35 U.S.C. 154(b) by 555 days.

(21) Appl. No.: 16/413,574

(22) Filed: May 15, 2019

(65) Prior Publication Data

US 2019/0352708 A1 Nov. 21, 2019

Related U.S. Application Data

(60) Provisional application No. 62/671,582, filed on May 15, 2018.

(51) Int. Cl.
| | | |
|---|---|---|
| *C12Q 1/6869* | (2018.01) | |
| *C12Q 1/6855* | (2018.01) | |
| *C12Q 1/686* | (2018.01) | |

(52) U.S. Cl.
CPC ........... *C12Q 1/6869* (2013.01); *C12Q 1/686* (2013.01); *C12Q 1/6855* (2013.01); *C12Q 2525/173* (2013.01); *C12Q 2533/101* (2013.01); *C12Q 2533/107* (2013.01); *C12Q 2563/159* (2013.01); *C12Q 2563/161* (2013.01); *C12Q 2563/185* (2013.01); *C12Q 2565/514* (2013.01)

(58) Field of Classification Search
CPC .... C12Q 1/6869; C12Q 1/6855; C12Q 1/686; C12Q 1/6816
See application file for complete search history.

(56) References Cited

U.S. PATENT DOCUMENTS

| | | | |
|---|---|---|---|
| 2016/0230235 A1* | 8/2016 | Ichiki | B01L 3/502761 |
| 2017/0192013 A1* | 7/2017 | Agresti | C12Q 1/6869 |
| 2018/0024139 A1* | 1/2018 | Peikon | C12Q 1/6804 506/4 |
| 2018/0251825 A1* | 9/2018 | Stoeckius | C12Q 1/6844 |
| 2018/0340939 A1* | 11/2018 | Gaublomme | C12Q 1/6823 |
| 2019/0025299 A1* | 1/2019 | Vigneault | C07K 14/7051 |
| 2019/0085324 A1* | 3/2019 | Regev | C12N 15/1093 |
| 2019/0361010 A1* | 11/2019 | Belhocine | G01N 33/5032 |

OTHER PUBLICATIONS

Bicknell et al, Amplification of Specific mRNA From a Single Human Renal Glomerulus, With an Approach to the Separation of Epithelial Cell mRNA, 1996, 180, 188-193. (Year: 1996).*

* cited by examiner

*Primary Examiner* — Narayan K Bhat
(74) *Attorney, Agent, or Firm* — Kwan & Olynick LLP

(57) ABSTRACT

According to various embodiments, a system and method for characterizing protein and nucleic acid content of a plurality of individual particles. The method includes encapsulating individual particles into compartments also containing analyte specific binding complements with oligonucleotide tags comprising a unique molecular identifier sequence, a sequence to identify the analyte specific binding complement, and a homology domain sequence. Allowing the oligonucleotide tags to hybridize on homology domain to form initial tag pairs, amplifying the tag pairs, using an enzyme to cut at the homology domain, allowing tags to re-hybridize, pooling the compartments, and sequencing. Finally, predicting co-encapsulated analytes by computational identification of clusters based on more frequently found oligonucleotide tag pairs.

20 Claims, 27 Drawing Sheets

| Number in each row, column index = number of times a UMI-UMI pair is observed | UMI_1 | UMI_2 | UMI_3 | UMI_4 | ..... | UMI_1000 | UMI_1050 | UMI_1051 | UMI_1052 | UMI_1053 | UMI_1054 | ..... | UMI_2050 | ..... | UMI_100000000 |
|---|---|---|---|---|---|---|---|---|---|---|---|---|---|---|---|
| UMI_1 | 2 | | | | | | | | | | | | | | |
| UMI_2 | 3 | 3 | | | | | | | | | | | | | |
| UMI_3 | 3 | 1 | 2 | | | | | | | | | | | | |
| UMI_4 | 4 | ..... | ..... | ..... | | | | | | | | | | | |
| ..... (UMIs from a true vesicle) | | | | | | | | | | | | | | | |
| UMI_1000 (UMI1-1000 are in a single vesicle) | 1 | 10 | 0 | 0 | ..... | | | | | | | | | | |
| ..... (UMIs not from a true vesicle – zero or low frequencies) | | | | | | | | | | | | | | | |
| UMI_1050 (example of UMI not from true vesicle – low frequency) | 0 | 0 | 0 | 0 | ..... | ..... | 0 | | | | | | | | |
| UMI_1051 | 0 | 0 | 0 | 0 | ..... | 0 | 1 | 5 | | | | | | | |
| UMI_1052 | 0 | 0 | 0 | 1 | ..... | 0 | 0 | 1 | 6 | | | | | | |
| UMI_1053 (includes a "noisy" link example, to UMI_4, that is not actually in same vesicle) | 0 | 0 | 0 | 0 | ..... | 0 | 0 | 3 | 1 | 1 | | | | | |
| UMI_1054 | 0 | 0 | 0 | 0 | ..... | 0 | 0 | 0 | 0 | 1 | 3 | | | | |
| ..... (UMIs not from a true vesicle) | 0 | 0 | 0 | 0 | ..... | 0 | 0 | 1 | 4 | 1 | 3 | ..... | | | |
| UMI_2050 (UMI1051-2050 are in a single vesicle) | | | | | | | | | | | | ..... | ..... | | |
| ..... (UMIs from more vesicles and from non-vesicles) | | | | | | | | | | | | | | | |
| UMI_100000000 (approximate number of total UMIs used in entire sequencing run) | 0 | 0 | 0 | 0 | ..... | 0 | 0 | 0 | | | | | | ..... | |

FIG. 3B

| Parameter | Values Tested |
|---|---|
| Number of Evs | 20, 100 |
| Number of RNA fragments/EV | 0.0, 0.15, 10.0 |
| Number of antibodies attached per EV | 1, 15 |
| Number of amplifications | 2, 5, 10, 15 |
| Percent of UMIs with noise | 0.0%, 0.1% 1.00%, 5.0%, 50.0%, 100.0% |
| Number of amplified replicates per UMI with noise | 1, 10, 2^10 |
| Network detection method | edge betweenness, walktrap |

FIG. 9

| Community detection Method | I: # of EVs | I: # RNAs per EV | I: # Antibodies per EV | I: Amplification rate | I: % of UMI IDs with at least 1 error | I: # of UMI replicates per UMI | I: % of all UMI replicates with error | I: Total UMI amplified replicates | I: Total UMI-UMI reads for sequencing | O: % wrong droplet assignment |
|---|---|---|---|---|---|---|---|---|---|---|
| E | 20 | 0 | 1 | 2 | 0 | 0 | 0 | 80 | 40 | 0 |
| E | 20 | 0 | 1 | 2 | 0 | 0 | 0 | 80 | 40 | 0 |
| E | 20 | 0 | 1 | 5 | 0 | 0 | 0 | 640 | 320 | 0 |
| E | 20 | 0 | 1 | 5 | 0 | 0 | 0 | 640 | 320 | 0 |
| E | 20 | 0 | 1 | 10 | 0 | 0 | 0 | 20480 | 10240 | 0 |
| E | 20 | 0 | 1 | 10 | 0 | 0 | 0 | 20480 | 10240 | 0 |
| E | 20 | 0 | 1 | 10 | 5 | 10 | 0.049 | 20490 | 10245 | 0 |
| E | 20 | 0 | 1 | 15 | 0 | 0 | 0 | 655360 | 327680 | 0 |
| E | 20 | 0 | 1 | 15 | 0 | 0 | 0 | 655360 | 327680 | 0 |
| E | 20 | 10 | 1 | 5 | 0 | 0 | 0 | 7040 | 3520 | 0 |
| E | 20 | 10 | 1 | 5 | 0 | 0 | 0 | 7040 | 3520 | 0 |
| E | 20 | 10 | 1 | 5 | 5 | 1 | 0.156 | 7051 | 3526 | 0 |
| E | 20 | 10 | 1 | 10 | 0 | 0 | 0 | 225280 | 112640 | 0 |
| E | 20 | 10 | 1 | 10 | 0 | 0 | 0 | 225280 | 112640 | 0 |
| E | 20 | 10 | 1 | 10 | 5 | 1 | 0.005 | 225291 | 112646 | 0 |
| E | 20 | 10 | 1 | 10 | 5 | 10 | 0.049 | 225390 | 112695 | 0 |
| E | 20 | 10 | 1 | 15 | 0 | 0 | 0 | 7208960 | 3604480 | 0 |
| E | 20 | 10 | 1 | 15 | 0 | 0 | 0 | 7208960 | 3604480 | 0 |
| E | 20 | 10 | 1 | 15 | 5 | 1 | 0 | 7208971 | 3604486 | 0 |
| E | 20 | 10 | 1 | 15 | 5 | 10 | 0.002 | 7209070 | 3604535 | 0 |
| E | 20 | 10 | 1 | 10 | 50 | 1 | 0.049 | 225390 | 112695 | 0 |
| E | 20 | 10 | 1 | 10 | 50 | 10 | 0.486 | 226380 | 113190 | 0 |

FIG. 10A

| E | 20 | 10 | 1 | 10 | 100 | 1 | 0.098 | 225500 | 112750 | 0 |
|---|---|---|---|---|---|---|---|---|---|---|
| E | 20 | 10 | 1 | 10 | 100 | 10 | 0.967 | 227480 | 113740 | 0 |
| E | 20 | 10 | 1 | 15 | 50 | 1 | 0.002 | 7209070 | 3604535 | 0 |
| E | 20 | 10 | 1 | 15 | 50 | 10 | 0.015 | 7210060 | 3605030 | 0 |
| E | 20 | 10 | 1 | 15 | 100 | 1 | 0.003 | 7209180 | 3604590 | 0 |
| E | 20 | 10 | 1 | 15 | 100 | 10 | 0.031 | 7211160 | 3605580 | 0 |
| E | 20 | 0 | 1 | 2 | 0 | 0 | 0 | 80 | 40 | 0 |
| E | 20 | 0 | 1 | 2 | 0 | 0 | 0 | 80 | 40 | 0 |
| E | 20 | 0 | 1 | 5 | 0 | 0 | 0 | 640 | 320 | 0 |
| E | 20 | 0 | 1 | 5 | 0 | 0 | 0 | 640 | 320 | 0 |
| E | 20 | 0 | 1 | 10 | 0 | 0 | 0 | 20480 | 10240 | 0 |
| E | 20 | 0 | 1 | 10 | 0 | 0 | 0 | 20480 | 10240 | 0 |
| E | 20 | 0 | 1 | 15 | 0 | 0 | 0 | 655360 | 327680 | 0 |
| E | 20 | 0 | 1 | 15 | 0 | 0 | 0 | 655360 | 327680 | 0 |
| E | 20 | 0 | 1 | 15 | 5 | 320 | 0.049 | 655680 | 327840 | 0 |
| E | 20 | 10 | 1 | 5 | 0 | 0 | 0 | 7040 | 3520 | 0 |
| E | 20 | 10 | 1 | 5 | 0 | 0 | 0 | 7040 | 3520 | 0 |
| E | 20 | 10 | 1 | 10 | 0 | 0 | 0 | 225280 | 112640 | 0 |
| E | 20 | 10 | 1 | 10 | 0 | 0 | 0 | 225280 | 112640 | 0 |
| E | 20 | 10 | 1 | 10 | 5 | 32 | 0.156 | 225632 | 112816 | 0 |
| E | 20 | 10 | 1 | 15 | 0 | 0 | 0 | 7208960 | 3604480 | 0 |
| E | 20 | 10 | 1 | 15 | 0 | 0 | 0 | 7208960 | 3604480 | 0 |
| E | 20 | 10 | 1 | 15 | 5 | 32 | 0.005 | 7209312 | 3604656 | 0 |
| E | 20 | 10 | 1 | 15 | 5 | 320 | 0.049 | 7212480 | 3606240 | 0 |
| E | 20 | 10 | 1 | 15 | 50 | 32 | 0.049 | 7212480 | 3606240 | 0 |
| E | 20 | 10 | 1 | 15 | 50 | 320 | 0.48 | 7244160 | 3622080 | 0 |

FIG. 10B

| | | | | | | | | | |
|---|---|---|---|---|---|---|---|---|---|
| | | | | | | 6 | | | |
| E | 20 | 10 | 1 | 15 | 100 | 32 | 0.098 | 7216000 | 3608000 | 0 |
| E | 20 | 10 | 1 | 15 | 100 | 320 | 0.967 | 7279360 | 3639680 | 0 |
| W | 20 | 0 | 15 | 5 | 0 | 0 | 0 | 9600 | 4800 | 0 |
| W | 20 | 0 | 15 | 5 | 0 | 0 | 0 | 9600 | 4800 | 0 |
| W | 20 | 0 | 15 | 5 | 5 | 1 | 0.156 | 9615 | 4808 | 0 |
| W | 20 | 0 | 15 | 10 | 0 | 0 | 0 | 307200 | 153600 | 0 |
| W | 20 | 0 | 15 | 10 | 0 | 0 | 0 | 307200 | 153600 | 0 |
| W | 20 | 0 | 15 | 10 | 5 | 1 | 0.005 | 307215 | 153608 | 0 |
| W | 20 | 0 | 15 | 10 | 5 | 10 | 0.049 | 307350 | 153675 | 0 |
| W | 20 | 0 | 15 | 15 | 0 | 0 | 0 | 9830400 | 4915200 | 0 |
| W | 20 | 0 | 15 | 15 | 0 | 0 | 0 | 9830400 | 4915200 | 0 |
| W | 20 | 0 | 15 | 15 | 5 | 1 | 0 | 9830415 | 4915208 | 0 |
| W | 20 | 0 | 15 | 15 | 5 | 10 | 0.002 | 9830550 | 4915275 | 0 |
| W | 20 | 0.15 | 15 | 5 | 0 | 0 | 0 | 9696 | 4848 | 0 |
| W | 20 | 0.15 | 15 | 5 | 0 | 0 | 0 | 9696 | 4848 | 0 |
| W | 20 | 0.15 | 15 | 5 | 5 | 1 | 0.156 | 9711.15 | 4856 | 0 |
| W | 20 | 0.15 | 15 | 10 | 0 | 0 | 0 | 310272 | 155136 | 0 |
| W | 20 | 0.15 | 15 | 10 | 0 | 0 | 0 | 310272 | 155136 | 0 |
| W | 20 | 0.15 | 15 | 10 | 5 | 1 | 0.005 | 310287.15 | 155144 | 0 |
| W | 20 | 0.15 | 15 | 10 | 5 | 10 | 0.049 | 310423.5 | 155212 | 0 |
| W | 20 | 0.15 | 15 | 15 | 0 | 0 | 0 | 9928704 | 4964352 | 0 |
| W | 20 | 0.15 | 15 | 15 | 0 | 0 | 0 | 9928704 | 4964352 | 0 |
| W | 20 | 0.15 | 15 | 15 | 5 | 1 | 0 | 9928719.15 | 4964360 | 0 |
| W | 20 | 0.15 | 15 | 15 | 5 | 10 | 0.002 | 9928855.5 | 4964428 | 0 |
| E | 20 | 0 | 15 | 10 | 50 | 1 | 0.04 | 307350 | 153675 | 0 |

FIG. 10C

| | | | | | | | 9 | | | |
|---|---|---|---|---|---|---|---|---|---|---|
| E | 20 | 0 | 15 | 10 | 50 | 10 | 0.486 | 308700 | 154350 | 0 |
| E | 20 | 0 | 15 | 10 | 100 | 1 | 0.098 | 307500 | 153750 | 0 |
| E | 20 | 0 | 15 | 15 | 50 | 1 | 0.002 | 9830550 | 4915275 | 0 |
| E | 20 | 0 | 15 | 15 | 50 | 10 | 0.015 | 9831900 | 4915950 | 0 |
| E | 20 | 0 | 15 | 15 | 100 | 1 | 0.003 | 9830700 | 4915350 | 0 |
| E | 20 | 0 | 15 | 15 | 100 | 10 | 0.031 | 9833400 | 4916700 | 0 |
| E | 20 | 0.15 | 15 | 10 | 50 | 1 | 0.049 | 310423.5 | 155212 | 0 |
| E | 20 | 0.15 | 15 | 10 | 50 | 10 | 0.486 | 311787 | 155894 | 0 |
| E | 20 | 0.15 | 15 | 10 | 100 | 1 | 0.098 | 310575 | 155288 | 0 |
| E | 20 | 0.15 | 15 | 15 | 50 | 1 | 0.002 | 9928855.5 | 4964428 | 0 |
| E | 20 | 0.15 | 15 | 15 | 50 | 10 | 0.015 | 9930219 | 4965110 | 0 |
| E | 20 | 0.15 | 15 | 15 | 100 | 1 | 0.003 | 9929007 | 4964504 | 0 |
| E | 20 | 0.15 | 15 | 15 | 100 | 10 | 0.031 | 9931734 | 4965867 | 0 |
| W | 20 | 0 | 1 | 2 | 0 | 0 | 0 | 80 | 40 | 0 |
| W | 20 | 0 | 1 | 2 | 0 | 0 | 0 | 80 | 40 | 0 |
| W | 20 | 0 | 1 | 5 | 0 | 0 | 0 | 640 | 320 | 0 |
| W | 20 | 0 | 1 | 5 | 0 | 0 | 0 | 640 | 320 | 0 |
| W | 20 | 0 | 1 | 5 | 5 | 1 | 0.156 | 641 | 320 | 0 |
| W | 20 | 0 | 1 | 5 | 5 | 10 | 1.538 | 650 | 325 | 0 |
| W | 20 | 0 | 1 | 10 | 0 | 0 | 0 | 20480 | 10240 | 0 |
| W | 20 | 0 | 1 | 10 | 0 | 0 | 0 | 20480 | 10240 | 0 |
| W | 20 | 0 | 1 | 15 | 0 | 0 | 0 | 655360 | 327680 | 0 |

FIG. 10D

| | | | | | | | | | |
|---|---|---|---|---|---|---|---|---|---|
| W | 20 | 0 | 1 | 15 | 0 | 0 | 0 | 655360 | 327680 | 0 |
| W | 20 | 0 | 1 | 15 | 5 | 1 | 0 | 655361 | 327680 | 0 |
| W | 20 | 10 | 1 | 5 | 0 | 0 | 0 | 7040 | 3520 | 0 |
| W | 20 | 10 | 1 | 5 | 0 | 0 | 0 | 7040 | 3520 | 0 |
| W | 20 | 10 | 1 | 5 | 5 | 1 | 0.156 | 7051 | 3526 | 0 |
| W | 20 | 10 | 1 | 10 | 0 | 0 | 0 | 225280 | 112640 | 0 |
| W | 20 | 10 | 1 | 10 | 0 | 0 | 0 | 225280 | 112640 | 0 |
| W | 20 | 10 | 1 | 10 | 5 | 1 | 0.005 | 225291 | 112646 | 0 |
| W | 20 | 10 | 1 | 10 | 5 | 10 | 0.049 | 225390 | 112695 | 0 |
| W | 20 | 10 | 1 | 15 | 0 | 0 | 0 | 7208960 | 3604480 | 0 |
| W | 20 | 10 | 1 | 15 | 0 | 0 | 0 | 7208960 | 3604480 | 0 |
| W | 20 | 10 | 1 | 15 | 5 | 1 | 0 | 7208971 | 3604486 | 0 |
| W | 20 | 10 | 1 | 15 | 5 | 10 | 0.002 | 7209070 | 3604535 | 0 |
| W | 20 | 0 | 1 | 15 | 50 | 1 | 0.002 | 655370 | 327685 | 0 |
| W | 20 | 0 | 1 | 15 | 100 | 1 | 0.003 | 655380 | 327690 | 0 |
| W | 20 | 10 | 1 | 10 | 50 | 1 | 0.049 | 225390 | 112695 | 0 |
| W | 20 | 10 | 1 | 10 | 50 | 10 | 0.486 | 226380 | 113190 | 0 |
| W | 20 | 10 | 1 | 10 | 100 | 1 | 0.098 | 225500 | 112750 | 0 |
| W | 20 | 10 | 1 | 10 | 100 | 10 | 0.967 | 227480 | 113740 | 0 |
| W | 20 | 10 | 1 | 15 | 50 | 1 | 0.002 | 7209070 | 3604535 | 0 |
| W | 20 | 10 | 1 | 15 | 50 | 10 | 0.015 | 7210060 | 3605030 | 0 |
| W | 20 | 10 | 1 | 15 | 100 | 1 | 0.003 | 7209180 | 3604590 | 0 |
| W | 20 | 10 | 1 | 15 | 100 | 10 | 0.031 | 7211160 | 3605580 | 0 |
| W | 20 | 0 | 1 | 2 | 0 | 0 | 0 | 80 | 40 | 0 |

FIG. 10E

| | | | | | | | | | |
|---|---|---|---|---|---|---|---|---|---|
| W | 20 | 0 | 1 | 5 | 0 | 0 | 0 | 640 | 320 | 0 |
| W | 20 | 0 | 1 | 10 | 0 | 0 | 0 | 20480 | 10240 | 0 |
| W | 20 | 0 | 1 | 15 | 0 | 0 | 0 | 655360 | 327680 | 0 |
| W | 20 | 10 | 1 | 5 | 0 | 0 | 0 | 7040 | 3520 | 0 |
| W | 20 | 10 | 1 | 10 | 0 | 0 | 0 | 225280 | 112640 | 0 |
| W | 20 | 10 | 1 | 15 | 0 | 0 | 0 | 7208960 | 3604480 | 0 |
| W | 20 | 10 | 1 | 15 | 5 | 1024 | 0.156 | 7220224 | 3610112 | 0 |
| W | 20 | 0 | 15 | 10 | 50 | 1 | 0.049 | 307350 | 153675 | 0 |
| W | 20 | 0 | 15 | 10 | 50 | 10 | 0.486 | 308700 | 154350 | 0 |
| W | 20 | 0 | 15 | 10 | 100 | 1 | 0.098 | 307500 | 153750 | 0 |
| W | 20 | 0 | 15 | 15 | 50 | 1 | 0.002 | 9830550 | 4915275 | 0 |
| W | 20 | 0 | 15 | 15 | 50 | 10 | 0.015 | 9831900 | 4915950 | 0 |
| W | 20 | 0 | 15 | 15 | 100 | 1 | 0.003 | 9830700 | 4915350 | 0 |
| W | 20 | 0 | 15 | 15 | 100 | 10 | 0.031 | 9833400 | 4916700 | 0 |
| W | 20 | 0.15 | 15 | 10 | 50 | 1 | 0.049 | 310423.5 | 155212 | 0 |
| W | 20 | 0.15 | 15 | 10 | 50 | 10 | 0.486 | 311787 | 155894 | 0 |
| W | 20 | 0.15 | 15 | 10 | 100 | 1 | 0.098 | 310575 | 155288 | 0 |
| W | 20 | 0.15 | 15 | 15 | 50 | 1 | 0.002 | 9928855.5 | 4964428 | 0 |
| W | 20 | 0.15 | 15 | 15 | 50 | 10 | 0.015 | 9930219 | 4965110 | 0 |
| W | 20 | 0.15 | 15 | 15 | 100 | 1 | 0.003 | 9929007 | 4964504 | 0 |
| W | 20 | 0.15 | 15 | 15 | 100 | 10 | 0.031 | 9931734 | 4965867 | 0 |
| W | 20 | 0 | 15 | 5 | 0 | 0 | 0 | 9600 | 4800 | 0 |
| W | 20 | 0 | 15 | 10 | 0 | 0 | 0 | 307200 | 153600 | 0 |

FIG. 10F

| | | | | | | | | | |
|---|---|---|---|---|---|---|---|---|---|
| W | 20 | 0 | 15 | 15 | 0 | 0 | 0 | 9830400 | 4915200 | 0 |
| W | 20 | 0 | 15 | 15 | 5 | 1024 | 0.156 | 9845760 | 4922880 | 0 |
| W | 20 | 0.15 | 15 | 5 | 0 | 0 | 0 | 9696 | 4848 | 0 |
| W | 20 | 0.15 | 15 | 10 | 0 | 0 | 0 | 310272 | 155136 | 0 |
| W | 20 | 0.15 | 15 | 15 | 0 | 0 | 0 | 9928704 | 4964352 | 0 |
| W | 20 | 0.15 | 15 | 15 | 5 | 1024 | 0.156 | 9944217.6 | 4972109 | 0 |
| W | 100 | 0.15 | 15 | 10 | 1 | 10 | 0.01 | 1551511.5 | 775756 | 0 |
| W | 100 | 0.15 | 15 | 10 | 0.1 | 10 | 0.001 | 1551375.1 | 775688 | 0 |
| W | 100 | 0.15 | 50 | 10 | 5 | 10 | 0.049 | 5137867.5 | 2568934 | 1.8 |
| W | 100 | 0.15 | 15 | 10 | 10 | 10 | 0.098 | 1552875 | 776438 | 1.9 |
| W | 100 | 0.15 | 50 | 10 | 10 | 10 | 0.098 | 5140375 | 2570188 | 2.5 |
| W | 100 | 0.15 | 15 | 10 | 0.1 | 1024 | 0.1 | 1552911.36 | 776456 | 4.6 |
| W | 20 | 10 | 1 | 5 | 5 | 10 | 1.538 | 7150 | 3575 | 5 |
| W | 100 | 0.15 | 15 | 10 | 50 | 10 | 0.486 | 1558935 | 779468 | 7.6 |
| W | 100 | 0.15 | 15 | 10 | 10 | 1024 | 9.091 | 1706496 | 853248 | 7.9 |
| E | 20 | 0 | 1 | 5 | 5 | 32 | 4.762 | 672 | 336 | 8 |
| W | 100 | 0.15 | 15 | 10 | 50 | 1024 | 33.333 | 2327040 | 1163520 | 8.6 |
| E | 20 | 0.15 | 15 | 15 | 50 | 1024 | 1.538 | 10083840 | 5041920 | 9.3 |
| E | 20 | 10 | 1 | 10 | 5 | 320 | 1.538 | 228800 | 114400 | 9.6 |
| W | 20 | 0 | 15 | 10 | 100 | 10 | 0.967 | 310200 | 155100 | 9.7 |
| W | 20 | 0.15 | 15 | 10 | 100 | 10 | 0.967 | 313302 | 156651 | 10.2 |
| W | 20 | 0 | 15 | 15 | 50 | 1024 | 1.538 | 9984000 | 4992000 | 10.2 |

FIG. 10G

| | | | | | | | | | |
|---|---|---|---|---|---|---|---|---|---|
| E | 20 | 10 | 1 | 5 | 5 | 10 | 1.538 | 7150 | 3575 | 10.3 |
| E | 20 | 0.15 | 15 | 15 | 100 | 1024 | 3.03 | 10238976 | 5119488 | 10.6 |
| W | 20 | 0.15 | 15 | 5 | 5 | 10 | 1.538 | 9847.5 | 4924 | 11 |
| E | 20 | 0 | 1 | 5 | 5 | 10 | 1.538 | 650 | 325 | 11.1 |
| E | 20 | 0.15 | 15 | 10 | 100 | 10 | 0.967 | 313302 | 156651 | 11.1 |
| W | 20 | 10 | 1 | 15 | 50 | 1024 | 1.538 | 7321600 | 3660800 | 11.4 |
| E | 20 | 0 | 15 | 10 | 100 | 10 | 0.967 | 310200 | 155100 | 11.5 |
| W | 20 | 0 | 1 | 10 | 5 | 1 | 0.005 | 20481 | 10240 | 11.5 |
| E | 20 | 0 | 15 | 5 | 50 | 1 | 1.538 | 9750 | 4875 | 12 |
| W | 20 | 0 | 15 | 5 | 5 | 10 | 1.538 | 9750 | 4875 | 12.3 |
| E | 20 | 0 | 1 | 5 | 5 | 320 | 33.333 | 960 | 480 | 12.5 |
| E | 20 | 0 | 15 | 5 | 100 | 1 | 3.03 | 9900 | 4950 | 12.7 |
| W | 20 | 0 | 1 | 15 | 5 | 10 | 0.002 | 655370 | 327685 | 13.3 |
| W | 20 | 0 | 1 | 15 | 5 | 1024 | 0.156 | 656384 | 328192 | 13.3 |
| E | 20 | 10 | 1 | 10 | 50 | 32 | 1.538 | 228800 | 114400 | 13.4 |
| W | 20 | 0.15 | 15 | 5 | 100 | 1 | 3.03 | 9999 | 5000 | 13.4 |
| E | 20 | 0 | 1 | 15 | 5 | 1 | 0 | 655361 | 327680 | 13.6 |
| W | 20 | 0 | 1 | 10 | 5 | 1024 | 4.762 | 21504 | 10752 | 13.6 |
| W | 20 | 0.15 | 15 | 5 | 50 | 1 | 1.538 | 9847.5 | 4924 | 13.7 |
| W | 20 | 0.15 | 15 | 5 | 100 | 10 | 23.81 | 12726 | 6363 | 13.7 |
| W | 20 | 0 | 15 | 5 | 50 | 1024 | 94.118 | 163200 | 81600 | 13.7 |
| W | 20 | 0 | 15 | 5 | 100 | 10 | 23.8 | 12600 | 6300 | 13.9 |

FIG. 10H

|   |   |   |   |   |   | 1 |   |   |   |
|---|---|---|---|---|---|---|---|---|---|
| E | 20 | 0.15 | 15 | 10 | 50 | 1024 | 33.333 | 465408 | 232704 | 14 |
| W | 20 | 0 | 15 | 5 | 50 | 1 | 1.538 | 9750 | 4875 | 14.1 |
| W | 20 | 0.15 | 15 | 5 | 5 | 1024 | 61.538 | 25209.6 | 12605 | 14.2 |
| W | 20 | 0.15 | 15 | 10 | 5 | 1024 | 4.762 | 325785.6 | 162893 | 14.2 |
| E | 20 | 0 | 15 | 15 | 50 | 1024 | 1.538 | 9984000 | 4992000 | 14.4 |
| W | 20 | 0 | 15 | 5 | 100 | 1024 | 96.97 | 316800 | 158400 | 14.7 |
| W | 20 | 0.15 | 15 | 15 | 50 | 1024 | 1.538 | 10083840 | 5041920 | 14.7 |
| E | 20 | 0.15 | 15 | 5 | 100 | 10 | 23.81 | 12726 | 6363 | 14.8 |
| E | 20 | 0 | 15 | 5 | 100 | 1024 | 96.97 | 316800 | 158400 | 14.8 |
| W | 20 | 0 | 15 | 5 | 5 | 1024 | 61.538 | 24960 | 12480 | 14.9 |
| E | 20 | 0 | 15 | 10 | 100 | 1024 | 50 | 614400 | 307200 | 14.9 |
| E | 20 | 0 | 15 | 5 | 50 | 10 | 13.514 | 11100 | 5550 | 15 |
| E | 20 | 0.15 | 15 | 5 | 50 | 1 | 1.538 | 9847.5 | 4924 | 15.2 |
| W | 20 | 0.15 | 15 | 10 | 100 | 1024 | 50 | 620544 | 310272 | 15.2 |
| E | 20 | 0 | 15 | 5 | 50 | 1024 | 94.118 | 163200 | 81600 | 15.2 |
| E | 20 | 10 | 1 | 5 | 100 | 1 | 3.03 | 7260 | 3630 | 15.3 |
| W | 20 | 0.15 | 15 | 5 | 50 | 1024 | 94.118 | 164832 | 82416 | 15.3 |
| E | 20 | 0 | 15 | 15 | 100 | 1024 | 3.03 | 10137600 | 5068800 | 15.3 |
| E | 20 | 0 | 1 | 15 | 5 | 32 | 0.005 | 655392 | 327696 | 15.4 |
| W | 20 | 0 | 15 | 5 | 50 | 10 | 13.514 | 11100 | 5550 | 15.4 |
| W | 20 | 10 | 1 | 5 | 50 | 1024 | 94.118 | 119680 | 59840 | 15.5 |

FIG. 10I

| W | 20 | 0 | 15 | 10 | 50 | 1024 | 33.333 | 460800 | 230400 | 15.5 |
|---|---|---|---|---|---|---|---|---|---|---|
| W | 20 | 0.15 | 15 | 15 | 100 | 1024 | 3.03 | 10238976 | 5119488 | 15.5 |
| W | 20 | 0 | 15 | 15 | 100 | 1024 | 3.03 | 10137600 | 5068800 | 15.6 |
| E | 20 | 0 | 15 | 10 | 50 | 1024 | 33.333 | 460800 | 230400 | 15.7 |
| E | 20 | 0.15 | 15 | 10 | 100 | 1024 | 50 | 620544 | 310272 | 15.7 |
| E | 20 | 0 | 1 | 10 | 50 | 10 | 0.486 | 20580 | 10290 | 15.8 |
| E | 20 | 10 | 1 | 5 | 50 | 1 | 1.538 | 7150 | 3575 | 15.8 |
| E | 20 | 0 | 1 | 2 | 5 | 320 | 80 | 400 | 200 | 15.8 |
| E | 20 | 0 | 1 | 10 | 5 | 320 | 1.538 | 20800 | 10400 | 15.8 |
| E | 20 | 10 | 1 | 5 | 50 | 320 | 83.333 | 42240 | 21120 | 15.8 |
| W | 20 | 10 | 1 | 10 | 50 | 1024 | 33.333 | 337920 | 168960 | 15.8 |
| E | 20 | 0.15 | 15 | 5 | 100 | 1024 | 96.97 | 319968 | 159984 | 15.8 |
| E | 20 | 0 | 15 | 5 | 100 | 10 | 23.81 | 12600 | 6300 | 15.9 |
| W | 20 | 10 | 1 | 5 | 100 | 10 | 23.81 | 9240 | 4620 | 15.9 |
| W | 20 | 0 | 15 | 10 | 5 | 1024 | 4.762 | 322560 | 161280 | 15.9 |
| E | 20 | 0.15 | 15 | 5 | 100 | 1 | 3.03 | 9999 | 5000 | 16 |
| W | 20 | 0.15 | 15 | 5 | 100 | 1024 | 96.97 | 319968 | 159984 | 16.1 |
| W | 20 | 0.15 | 15 | 5 | 50 | 10 | 13.514 | 11211 | 5606 | 16.2 |
| W | 20 | 0 | 15 | 5 | 100 | 1 | 3.03 | 9900 | 4950 | 16.3 |
| W | 20 | 10 | 1 | 5 | 5 | 1024 | 61.538 | 18304 | 9152 | 16.6 |
| W | 20 | 10 | 1 | 5 | 50 | 1 | 1.538 | 7150 | 3575 | 16.7 |
| E | 20 | 10 | 1 | 5 | 50 | 10 | 13.514 | 8140 | 4070 | 16.8 |
| E | 20 | 10 | 1 | 5 | 100 | 320 | 90.9 | 77440 | 38720 | 16.9 |

FIG. 10J

| | | | | | | | 09 | | | |
|---|---|---|---|---|---|---|---|---|---|---|
| W | 20 | 0 | 15 | 10 | 100 | 1024 | 50 | 614400 | 307200 | 17 |
| W | 20 | 10 | 1 | 15 | 100 | 1024 | 3.03 | 7434240 | 3717120 | 17.1 |
| E | 20 | 0.15 | 15 | 5 | 50 | 1024 | 94.118 | 164832 | 82416 | 17.1 |
| E | 20 | 10 | 1 | 5 | 100 | 10 | 23.81 | 9240 | 4620 | 17.4 |
| W | 20 | 0 | 1 | 2 | 5 | 1 | 1.235 | 81 | 40 | 17.4 |
| E | 20 | 10 | 1 | 5 | 5 | 32 | 4.762 | 7392 | 3696 | 17.5 |
| E | 20 | 10 | 1 | 5 | 5 | 320 | 33.333 | 10560 | 5280 | 17.5 |
| E | 20 | 0 | 1 | 2 | 5 | 1 | 1.235 | 81 | 40 | 17.6 |
| E | 20 | 0 | 1 | 2 | 5 | 32 | 28.571 | 112 | 56 | 17.6 |
| E | 20 | 10 | 1 | 10 | 50 | 320 | 13.514 | 260480 | 130240 | 17.7 |
| E | 20 | 10 | 1 | 10 | 100 | 32 | 3.03 | 232320 | 116160 | 17.7 |
| W | 20 | 10 | 1 | 5 | 50 | 10 | 13.514 | 8140 | 4070 | 17.9 |
| W | 20 | 10 | 1 | 10 | 5 | 1024 | 4.762 | 236544 | 118272 | 18.1 |
| E | 20 | 0.15 | 1 | 15 | 50 | 32 | 0.049 | 754032 | 377016 | 18.2 |
| W | 20 | 0 | 1 | 5 | 5 | 1024 | 61.538 | 1664 | 832 | 18.8 |
| E | 20 | 0 | 1 | 5 | 5 | 1 | 0.156 | 641 | 320 | 19 |
| E | 20 | 0.15 | 15 | 5 | 50 | 10 | 13.514 | 11211 | 5606 | 19 |
| W | 20 | 10 | 1 | 5 | 100 | 1024 | 96.97 | 232320 | 116160 | 19 |
| E | 20 | 10 | 1 | 10 | 100 | 320 | 23.81 | 295680 | 147840 | 19.2 |
| W | 20 | 10 | 1 | 10 | 100 | 1024 | 50 | 450560 | 225280 | 19.5 |
| E | 20 | 0 | 1 | 10 | 5 | 32 | 0.156 | 20512 | 10256 | 20 |

FIG. 10K

| | | | | | | | | | |
|---|---|---|---|---|---|---|---|---|---|
| W | 20 | 10 | 1 | 5 | 100 | 1 | 3.03 | 7260 | 3630 | 20 |
| W | 20 | 0.15 | 15 | 10 | 50 | 1024 | 33.333 | 465408 | 232704 | 20.5 |
| E | 20 | 10 | 1 | 5 | 100 | 32 | 50 | 14080 | 7040 | 20.9 |
| E | 20 | 0 | 1 | 15 | 5 | 10 | 0.002 | 655370 | 327685 | 21.1 |
| E | 20 | 10 | 1 | 5 | 50 | 32 | 33.333 | 10560 | 5280 | 21.3 |
| E | 20 | 0 | 1 | 10 | 5 | 1 | 0.005 | 20481 | 10240 | 21.4 |
| W | 20 | 0 | 1 | 2 | 5 | 10 | 11.111 | 90 | 45 | 21.4 |
| W | 20 | 0 | 1 | 10 | 50 | 1 | 0.049 | 20490 | 10245 | 21.7 |
| W | 20 | 0 | 1 | 2 | 5 | 1024 | 92.754 | 1104 | 552 | 22.2 |
| W | 20 | 0 | 1 | 15 | 50 | 10 | 0.015 | 655460 | 327730 | 22.7 |
| E | 20 | 0 | 1 | 10 | 50 | 32 | 1.538 | 20800 | 10400 | 26.3 |
| W | 20 | 0.15 | 1 | 15 | 50 | 1024 | 1.538 | 765440 | 382720 | 26.9 |
| E | 20 | 0 | 1 | 2 | 5 | 10 | 11.111 | 90 | 45 | 27.3 |
| W | 20 | 0 | 1 | 10 | 5 | 10 | 0.049 | 20490 | 10245 | 30.8 |
| E | 20 | 0 | 1 | 15 | 50 | 10 | 0.015 | 655460 | 327730 | 31.8 |
| W | 20 | 0 | 1 | 15 | 100 | 10 | 0.031 | 655560 | 327780 | 31.8 |
| W | 20 | 0 | 1 | 5 | 50 | 10 | 13.514 | 740 | 370 | 36 |
| W | 20 | 0 | 1 | 10 | 50 | 10 | 0.486 | 20580 | 10290 | 40 |
| E | 20 | 0 | 1 | 15 | 50 | 1 | 0.002 | 655370 | 327685 | 42.9 |
| W | 20 | 0 | 1 | 2 | 50 | 1 | 11.111 | 90 | 45 | 42.9 |
| E | 20 | 0.15 | 1 | 10 | 50 | 32 | 1.538 | 23920 | 11960 | 47.8 |

FIG. 10L

| | | | | | | | | | |
|---|---|---|---|---|---|---|---|---|---|
| W | 20 | 0 | 1 | 10 | 100 | 1 | 0.098 | 20500 | 10250 | 52 |
| E | 20 | 0.15 | 1 | 5 | 100 | 320 | 90.909 | 8096 | 4048 | 52.8 |
| E | 20 | 0.15 | 1 | 2 | 50 | 320 | 97.561 | 3772 | 1886 | 54.5 |
| W | 20 | 0 | 1 | 5 | 50 | 1 | 1.538 | 650 | 325 | 56.5 |
| W | 20 | 0.15 | 1 | 15 | 100 | 1024 | 3.03 | 777216 | 388608 | 57.7 |
| E | 20 | 0 | 1 | 5 | 50 | 32 | 33.333 | 960 | 480 | 60 |
| E | 20 | 0.15 | 1 | 10 | 100 | 320 | 23.81 | 30912 | 15456 | 60.9 |
| W | 20 | 0 | 1 | 2 | 50 | 1024 | 99.225 | 10320 | 5160 | 61.1 |
| E | 20 | 0.15 | 1 | 15 | 50 | 320 | 0.486 | 757344 | 378672 | 61.9 |
| W | 20 | 0.15 | 1 | 2 | 50 | 1024 | 99.225 | 11868 | 5934 | 62.1 |
| W | 20 | 0 | 1 | 15 | 100 | 1024 | 3.03 | 675840 | 337920 | 64.3 |
| E | 20 | 0 | 1 | 5 | 50 | 10 | 13.514 | 740 | 370 | 66.7 |
| E | 20 | 0 | 1 | 15 | 50 | 32 | 0.049 | 655680 | 327840 | 66.7 |
| E | 20 | 0 | 1 | 2 | 50 | 32 | 80 | 400 | 200 | 70.8 |
| E | 20 | 0.15 | 1 | 5 | 50 | 320 | 83.333 | 4416 | 2208 | 70.8 |
| E | 20 | 10 | 1 | 2 | 0 | 0 | 0 | 880 | 440 | 71.4 |
| E | 20 | 0 | 1 | 2 | 50 | 1 | 11.111 | 90 | 45 | 71.4 |
| E | 20 | 0 | 1 | 15 | 100 | 10 | 0.031 | 655560 | 327780 | 71.4 |
| E | 20 | 0 | 1 | 5 | 100 | 32 | 50 | 1280 | 640 | 71.4 |
| W | 20 | 0 | 1 | 15 | 50 | 1024 | 1.538 | 665600 | 332800 | 71.4 |
| E | 20 | 0.15 | 1 | 2 | 100 | 320 | 98.765 | 7452 | 3726 | 71.9 |
| E | 20 | 0.15 | 1 | 10 | 50 | 320 | 13.514 | 27232 | 13616 | 72.7 |

FIG. 10M

| | | | | | | | | | |
|---|---|---|---|---|---|---|---|---|---|
| E | 20 | 0 | 1 | 10 | 50 | 1 | 0.049 | 20490 | 10245 | 73.3 |
| E | 20 | 0 | 1 | 10 | 50 | 320 | 13.514 | 23680 | 11840 | 73.7 |
| W | 20 | 0 | 1 | 2 | 100 | 1 | 20 | 100 | 50 | 73.7 |
| E | 20 | 0 | 1 | 2 | 50 | 10 | 55.556 | 180 | 90 | 76.2 |
| W | 20 | 0 | 1 | 5 | 100 | 1 | 3.03 | 660 | 330 | 76.5 |
| E | 20 | 10 | 1 | 2 | 0 | 0 | 0 | 880 | 440 | 76.7 |
| E | 20 | 0 | 1 | 5 | 100 | 320 | 90.909 | 7040 | 3520 | 78.9 |
| W | 20 | 10 | 1 | 2 | 100 | 10 | 71.429 | 3080 | 1540 | 78.9 |
| E | 20 | 0 | 1 | 5 | 100 | 10 | 23.81 | 840 | 420 | 80 |
| E | 20 | 0.15 | 1 | 15 | 100 | 320 | 0.967 | 761024 | 380512 | 81 |
| E | 20 | 0 | 1 | 15 | 50 | 320 | 0.486 | 658560 | 329280 | 81.2 |
| W | 20 | 10 | 1 | 2 | 0 | 0 | 0 | 880 | 440 | 81.4 |
| W | 20 | 10 | 1 | 2 | 5 | 10 | 11.111 | 990 | 495 | 81.7 |
| W | 20 | 10 | 1 | 2 | 5 | 1 | 1.235 | 891 | 446 | 81.8 |
| W | 20 | 0.15 | 1 | 5 | 50 | 1024 | 94.118 | 12512 | 6256 | 81.8 |
| W | 20 | 0.15 | 1 | 5 | 100 | 1024 | 96.97 | 24288 | 12144 | 82.6 |
| E | 20 | 10 | 1 | 2 | 50 | 1 | 11.111 | 990 | 495 | 82.7 |
| E | 20 | 10 | 1 | 2 | 0 | 0 | 0 | 880 | 440 | 82.7 |
| E | 20 | 10 | 1 | 2 | 5 | 1 | 1.235 | 891 | 446 | 83.5 |
| E | 20 | 0.15 | 1 | 2 | 50 | 32 | 80 | 460 | 230 | 84 |
| E | 20 | 10 | 1 | 2 | 100 | 10 | 71.429 | 3080 | 1540 | 84.2 |
| W | 20 | 10 | 1 | 2 | 0 | 0 | 0 | 880 | 440 | 84.2 |
| W | 20 | 0 | 1 | 10 | 50 | 1024 | 33.333 | 30720 | 15360 | 84.2 |

FIG. 10N

| | | | | | | | | | |
|---|---|---|---|---|---|---|---|---|---|
| E | 20 | 10 | 1 | 2 | 100 | 320 | 98.765 | 71280 | 35640 | 84.4 |
| E | 20 | 10 | 1 | 2 | 100 | 1 | 20 | 1100 | 550 | 84.5 |
| W | 20 | 10 | 1 | 2 | 5 | 1024 | 92.754 | 12144 | 6072 | 84.6 |
| W | 20 | 0 | 1 | 2 | 50 | 10 | 55.556 | 180 | 90 | 85 |
| E | 20 | 0.15 | 1 | 5 | 100 | 32 | 50 | 1472 | 736 | 85.2 |
| W | 20 | 10 | 1 | 2 | 50 | 10 | 55.556 | 1980 | 990 | 85.4 |
| E | 20 | 10 | 1 | 2 | 0 | 0 | 0 | 880 | 440 | 85.6 |
| E | 20 | 0 | 1 | 2 | 100 | 32 | 88.889 | 720 | 360 | 86.4 |
| E | 20 | 0 | 1 | 15 | 100 | 32 | 0.098 | 656000 | 328000 | 86.4 |
| E | 20 | 10 | 1 | 2 | 50 | 10 | 55.556 | 1980 | 990 | 86.6 |
| W | 20 | 10 | 1 | 2 | 0 | 0 | 0 | 880 | 440 | 87 |
| W | 20 | 0 | 1 | 5 | 100 | 1024 | 96.97 | 21120 | 10560 | 87 |
| E | 20 | 10 | 1 | 2 | 50 | 32 | 80 | 4400 | 2200 | 87.2 |
| E | 20 | 10 | 1 | 2 | 5 | 32 | 28.571 | 1232 | 616 | 87.4 |
| E | 20 | 0.15 | 1 | 10 | 100 | 32 | 3.03 | 24288 | 12144 | 87.5 |
| E | 20 | 0 | 1 | 2 | 100 | 1 | 20 | 100 | 50 | 88.2 |
| E | 20 | 0 | 1 | 5 | 50 | 1 | 1.538 | 650 | 325 | 88.9 |
| E | 20 | 0 | 1 | 5 | 50 | 320 | 83.333 | 3840 | 1920 | 89.5 |
| W | 20 | 0.15 | 1 | 10 | 50 | 1024 | 33.333 | 35328 | 17664 | 89.5 |
| E | 20 | 10 | 1 | 2 | 5 | 10 | 11.111 | 990 | 495 | 89.6 |
| W | 20 | 0.15 | 1 | 2 | 100 | 1024 | 99.611 | 23644 | 11822 | 89.7 |
| W | 20 | 10 | 1 | 2 | 50 | 1024 | 99.225 | 113520 | 56760 | 90.3 |
| E | 20 | 0.15 | 1 | 5 | 50 | 32 | 33.333 | 1104 | 552 | 90.9 |

FIG. 10O

| | | | | | | | | | |
|---|---|---|---|---|---|---|---|---|---|
| E | 20 | 0 | 1 | 15 | 100 | 1 | 0.003 | 655380 | 327690 | 91.3 |
| W | 20 | 10 | 1 | 2 | 50 | 1 | 11.111 | 990 | 495 | 91.3 |
| E | 20 | 10 | 1 | 2 | 50 | 320 | 97.561 | 36080 | 18040 | 91.7 |
| E | 20 | 10 | 1 | 2 | 5 | 320 | 80 | 4400 | 2200 | 92 |
| W | 20 | 0 | 1 | 2 | 100 | 10 | 71.429 | 280 | 140 | 92 |
| W | 20 | 10 | 1 | 2 | 100 | 1 | 20 | 1100 | 550 | 92.2 |
| E | 20 | 0.15 | 15 | 2 | 100 | 1 | 20 | 1515 | 758 | 92.7 |
| E | 20 | 0 | 1 | 2 | 50 | 320 | 97.561 | 3280 | 1640 | 92.9 |
| W | 20 | 0 | 15 | 2 | 0 | 0 | 0 | 1200 | 600 | 93.2 |
| E | 20 | 0 | 1 | 10 | 100 | 320 | 23.81 | 26880 | 13440 | 94.7 |
| E | 20 | 0 | 1 | 2 | 100 | 10 | 71.429 | 280 | 140 | 95.2 |
| E | 20 | 0.15 | 1 | 2 | 100 | 32 | 88.889 | 828 | 414 | 95.8 |
| W | 20 | 0.15 | 15 | 2 | 5 | 1 | 1.235 | 1227.15 | 614 | 97.1 |
| E | 20 | 0 | 15 | 2 | 100 | 1024 | 99.611 | 308400 | 154200 | 97.1 |
| W | 20 | 0 | 15 | 2 | 100 | 1024 | 99.611 | 308400 | 154200 | 97.2 |
| E | 20 | 0 | 15 | 2 | 50 | 1 | 11.111 | 1350 | 675 | 97.3 |
| E | 20 | 0.15 | 15 | 2 | 50 | 10 | 55.556 | 2727 | 1364 | 97.3 |
| W | 20 | 0 | 15 | 2 | 50 | 10 | 55.556 | 2700 | 1350 | 97.3 |
| E | 20 | 0 | 15 | 2 | 50 | 1024 | 99.225 | 154800 | 77400 | 97.3 |
| E | 20 | 0.15 | 15 | 2 | 100 | 10 | 71.429 | 4242 | 2121 | 97.5 |
| W | 20 | 0.15 | 15 | 2 | 50 | 1024 | 99.225 | 156348 | 78174 | 97.5 |
| E | 20 | 0 | 15 | 2 | 100 | 1 | 20 | 1500 | 750 | 97.6 |

FIG. 10P

| | | | | | | | | | |
|---|---|---|---|---|---|---|---|---|---|
| W | 20 | 0 | 15 | 2 | 50 | 1 | 11.111 | 1350 | 675 | 97.6 |
| W | 20 | 0.15 | 15 | 2 | 50 | 1 | 11.111 | 1363.5 | 682 | 97.6 |
| W | 20 | 0 | 15 | 2 | 50 | 1024 | 99.225 | 154800 | 77400 | 97.6 |
| W | 20 | 0.15 | 15 | 2 | 50 | 10 | 55.556 | 2727 | 1364 | 97.7 |
| W | 20 | 0.15 | 15 | 2 | 5 | 10 | 11.111 | 1363.5 | 682 | 97.9 |
| E | 20 | 0.15 | 15 | 2 | 100 | 1024 | 99.611 | 311484 | 155742 | 97.9 |
| E | 20 | 0 | 15 | 2 | 100 | 10 | 71.429 | 4200 | 2100 | 98 |
| W | 20 | 0.15 | 15 | 2 | 100 | 10 | 71.429 | 4242 | 2121 | 98 |
| E | 20 | 10 | 1 | 2 | 100 | 32 | 88.889 | 7920 | 3960 | 98.3 |
| W | 20 | 0.15 | 15 | 2 | 0 | 0 | 0 | 1212 | 606 | 99.3 |
| E | 20 | 0 | 1 | 5 | 100 | 1 | 3.03 | 660 | 330 | 100 |
| E | 20 | 0 | 1 | 10 | 100 | 1 | 0.098 | 20500 | 10250 | 100 |
| E | 20 | 0 | 1 | 10 | 100 | 10 | 0.967 | 20680 | 10340 | 100 |
| E | 20 | 0 | 1 | 2 | 100 | 320 | 98.765 | 6480 | 3240 | 100 |
| E | 20 | 0 | 1 | 10 | 100 | 32 | 3.03 | 21120 | 10560 | 100 |
| E | 20 | 0 | 1 | 15 | 100 | 320 | 0.967 | 661760 | 330880 | 100 |
| E | 20 | 0.15 | 1 | 15 | 100 | 32 | 0.098 | 754400 | 377200 | 100 |
| W | 20 | 0 | 15 | 2 | 0 | 0 | 0 | 1200 | 600 | 100 |
| W | 20 | 0 | 15 | 2 | 5 | 1 | 1.235 | 1215 | 608 | 100 |
| W | 20 | 0 | 15 | 2 | 5 | 10 | 11.111 | 1350 | 675 | 100 |
| W | 20 | 0.15 | 15 | 2 | 0 | 0 | 0 | 1212 | 606 | 100 |
| W | 20 | 0.15 | 15 | 2 | 0 | 0 | 0 | 1212 | 606 | 100 |
| E | 20 | 0 | 15 | 2 | 50 | 10 | 55.5 | 2700 | 1350 | 100 |

FIG. 10Q

|   |   |   |   |   |   |   | 56 |   |   |   |
|---|---|---|---|---|---|---|----|---|---|---|
| E | 20 | 0.15 | 15 | 2 | 50 | 1 | 11.111 | 1363.5 | 682 | 100 |
| W | 20 | 0 | 1 | 5 | 100 | 10 | 23.81 | 840 | 420 | 100 |
| W | 20 | 0 | 1 | 10 | 100 | 10 | 0.967 | 20680 | 10340 | 100 |
| W | 20 | 0 | 1 | 2 | 100 | 1024 | 99.611 | 20560 | 10280 | 100 |
| W | 20 | 0 | 1 | 5 | 50 | 1024 | 94.118 | 10880 | 5440 | 100 |
| W | 20 | 0 | 1 | 10 | 100 | 1024 | 50 | 40960 | 20480 | 100 |
| W | 20 | 0.15 | 1 | 10 | 100 | 1024 | 50 | 47104 | 23552 | 100 |
| W | 20 | 10 | 1 | 2 | 100 | 1024 | 99.611 | 226160 | 113080 | 100 |
| W | 20 | 0 | 15 | 2 | 100 | 1 | 20 | 1500 | 750 | 100 |
| W | 20 | 0 | 15 | 2 | 100 | 10 | 71.429 | 4200 | 2100 | 100 |
| W | 20 | 0.15 | 15 | 2 | 100 | 1 | 20 | 1515 | 758 | 100 |
| W | 20 | 0 | 15 | 2 | 0 | 0 | 0 | 1200 | 600 | 100 |
| W | 20 | 0 | 15 | 2 | 5 | 1024 | 92.754 | 16560 | 8280 | 100 |
| W | 20 | 0.15 | 15 | 2 | 5 | 1024 | 92.754 | 16725.6 | 8363 | 100 |
| W | 20 | 0.15 | 15 | 2 | 100 | 1024 | 99.611 | 311484 | 155742 | 100 |
| E | 20 | 0.15 | 15 | 2 | 50 | 1024 | 99.225 | 156348 | 78174 | 100 |

FIG. 10R

BARCODE-FREE SINGLE VESICLE MULTIPLEXED PROTEIN AND RNA ANALYSIS

CROSS-REFERENCE TO RELATED APPLICATIONS

This application claims the benefit of U.S. Provisional Application No. 62/671,582, entitled "BARCODE-FREE SINGLE VESICLE MULTIPLEXED PROTEIN AND RNA ANALYSIS," filed on Mar. 15, 2018, which is incorporated by reference herein in its entirety for all purposes

TECHNICAL FIELD

The present disclosure relates generally to extracellular vesicles and RNA analysis, specifically to the utilization of genetic sequencing technology to specifically characterize protein and/or nucleic acid content in single vesicles with high sensitivity.

BACKGROUND

Cells and extracellular vesicles (EVs) are often heterogenous populations varying widely in their characteristics. Even within a single cell type the presence of surface proteins and RNA can be quite different depending on many parameters including the cell's environment, point in cell cycle, historical environmental exposures, etc. Therefore it is extremely important to be able to analyze groups of vesicles at a single vesicle resolution. There exist technologies currently employed to do this, though most have a very poor ability to achieve multiplex detection, are near the limit of sensitivity, or are incapable of simultaneously characterizing protein and RNA. The most powerful method in terms of multiplexing, sensitivity, and the ability for simultaneous measurement of protein and de novo RNA sequencing is the use of oligonucleotide "barcoded" beads simultaneously encapsulated with a single cell or vesicle in droplets and processed with next gen sequencing (NGS).

Of particular interest is a specific subset of EVs, termed exosomes and characterized by the specific cell pathway in which they are emitted, are generally expected to be in the size range of 40-100 nm and are known to carry a mixture of protein, RNA and genomic DNA. The function of exosomes is not yet clearly known but they have been demonstrated to participate in cell-to-cell signaling as they are transferred between cells and influence the behavior of the receiving cell. One example of such a function is that exosomes are released from the cells when multivesicular endosomes (MVE) fuse with the cytoplasmic membrane to release their vesicle content from the cells instead of merging with a lysosome for degradation.

Researchers have shown that subpopulations of EVs may target or effect tissues differently. EV subpopulations are differentiated by one of many properties including, but not limited to: their electrostatic potential, their surface proteins, or their size. The ability for EVs to selectively target tissues is likely largely mediated by the accessible surface proteins which a receiving cell can interact with to either accept, ingest and process; or reject and return to circulation. Because of the small size, sheer number and great heterogeneity of EVs they have been difficult to characterize. This technology addresses this issue with increased sensitivity and multiplexing capability, thereby enabling the identification of EV subpopulations and their molecular cargo for discovery of potential therapeutic targets, targeting motifs for delivery vehicles, and precision diagnostics.

Single-Cell Droplet DNA barcoding and antibody labelling allows the potentially unlimited ability to profile very large numbers of signaling protein activation states in single cells. The key to the approach is the use of antibodies labeled with DNA sequences which, combined with the more commonly used droplet single cell DNA barcoding technology, followed by amplification and sequencing, results in NGS counts that reflect the abundance of an antibody binding to a particular cell. By using this technology, there is theoretically no limitation on minimum vesicle detectable size in comparison to alternative methods such as flow cytometry and the ability to detect vesicles less than 1 nm in size. For example, a 10 base pair label can generate 1 million barcodes, so theoretically one could probe for as many antibodies as are known to exist. However, current state of the art of single-cell droplet DNA barcoding and antibody labelling have claimed that the current practical limit with available sequencing technology and minimum required counts is approximately 200 antibodies, Additionally the sensitivity capabilities of Single-Cell Droplet DNA barcoding and antibody labelling exceed the physical limits of competing technologies. For example, the Helios CyTOF system (Fluidigm) can detect down to 350 antibodies/cell, and the FACSAria III Cell Sorter (BD) can detect 85 FITC molecules/particle according to manufacturer's' specification. With DNA antibody tags one can theoretically detect a single antibody per cell because the DNA tags are amplified from single-molecule templates.

Applying the existing, single cell measurement technologies to EVs means pushing their limits of performance. This is because EVs are more heterogeneous than cells in terms of surface proteins and internal molecular cargo, each EV is very small and contains few, if any, copies of a particular DNA, RNA or protein, and EVs are orders of magnitude more prevalent than cells. Therefore, there is a need for better and more efficient systems and methods for identifying EV subpopulations and payloads for potential targeted therapeutics.

The use of NGS and barcoded beads combined with DNA labelled antibodies is a powerful tool for single vesicle characterization though there are some current issues with translation of this approach from single cells to single vesicles. Current issues include: the availability of high quality barcoded antibodies (or aptamers), the need for microfluidic devices and easy to use droplet barcoding technology, reagent costs, sequencer operation costs, and the requirement for sufficient read depth to allow enough vesicles and antibodies to be sequenced.

One issue in particular pertains to a currently very wasteful step when using barcoded beads for single vesicle analysis that is due to the need to combine two poisson distributed entities: the barcodes, and the vesicles. Each entity must individually be diluted to the point that there will statistically be very rarely more than a single entity in a droplet when the solution is emulsified. Generally this means this extreme dilution results in 95% of droplets being empty and of no use in downstream sequencing. When the process then calls for the merging of two of these populations, the resulting droplets which successfully contain both a single barcode and a single vesicle are less than 0.25% of all droplets, compared to around 10% of droplets which have just one or the other, and then the rest of the droplets (approximately 89%) are completely empty. A droplet that only contains barcodes, or only contains vesicles, cannot be used for downstream sequencing. This negatively affects the use of reagents and wastes precious NGS reads in addition to being technically challenging to achieve.

Thus, there is a need for a method and system for characterizing surface protein and/or RNA or DNA content in single vesicles that avoids barcodes entirely by using unique molecular identifiers (UMI) on oligonucleotide labels introduced into the solution and co-encapsulated with single vesicles, thereby simplifying the sample preparation workflow and reducing complexity and cost to operate.

SUMMARY

The following presents a simplified summary of the disclosure in order to provide a basic understanding of certain embodiments of the disclosure. This summary is not an extensive overview of the disclosure and it does not identify key/critical elements of the disclosure or delineate the scope of the disclosure. Its sole purpose is to present some concepts disclosed herein in a simplified form as a prelude to the more detailed description that is presented later.

According to various embodiments, a system and method for characterizing protein and nucleic acid content of single vesicles without barcodes is provided. The method includes collecting and isolating exosomes, creating DNA-tagged antibodies and DNA-tags for nucleic acids, immunoprobing target vesicles with the DNA-tagged antibodies, adding the DNA-tags for nucleic acids, emulsifying the solution into droplets, adding PCR reagents, freeing labels from their antibodies, attaching antibody DNA-tags and intravesicular RNA to probes, synthesizing cDNA in droplet, amplifying using overlap extension PCR, cutting and mixing with restriction enzymes, breaking emulsions, purifying DNA, amplifying using a second round of PCR, creating a library, paired-end sequencing, and algorithmic prediction of single vesicle associated molecules.

These and other embodiments are described further below with reference to the figures.

BRIEF DESCRIPTION OF THE DRAWINGS

The disclosure may best be understood by reference to the following description taken in conjunction with the accompanying drawings, which illustrate particular embodiments of the present disclosure.

FIGS. 3A-3B illustrate an example of barcode-free single vesicle content reconstruction, in accordance with one or more embodiments.

BRIEF DESCRIPTION OF THE TABLES

Figure 1A:
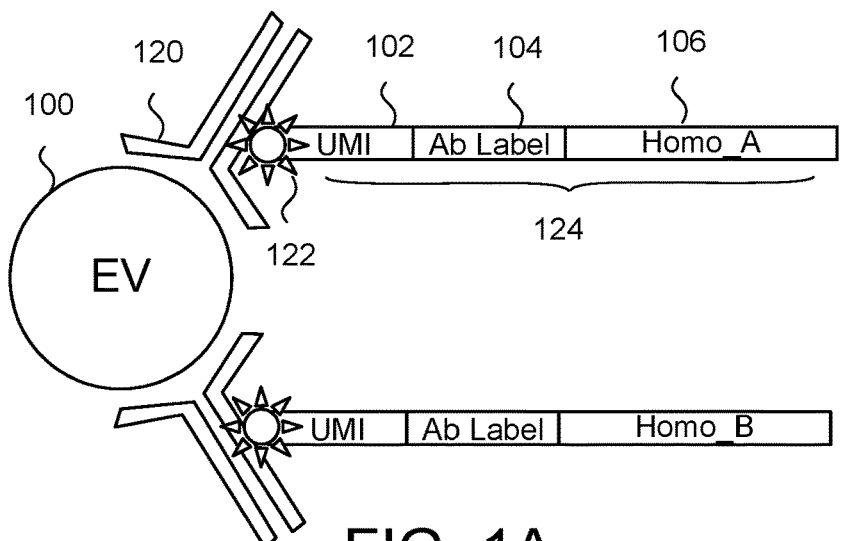
FIGS. 1A-1E illustrate a flow process for antibody labeling, in accordance with one or more embodiments.

Table 1 is a record of different parameters, and parameter values tested, during simulations run via a programming script that explores error rates in the computational demultiplexing single droplet (and thus EV) assignments.

Table 2 is the outputted results from the simulations run with the parameters and parameter values outlined in Table 1.

DESCRIPTION OF PARTICULAR EMBODIMENTS

Reference will now be made in detail to some specific examples of the present disclosure including the best modes contemplated by the inventors for carrying out the present disclosure. Examples of these specific embodiments are illustrated in the accompanying drawings. While the present disclosure is described in conjunction with these specific embodiments, it will be understood that it is not intended to limit the present disclosure to the described embodiments. On the contrary, it is intended to cover alternatives, modifications, and equivalents as may be included within the spirit and scope of the present disclosure as defined by the appended claims.

In the following description, numerous specific details are set forth in order to provide a thorough understanding of the present disclosure. Particular example embodiments of the present disclosure may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some embodiments include multiple iterations of a technique or multiple instantiations of a mechanism unless noted otherwise. Furthermore, the techniques and mechanisms of the present disclosure will sometimes describe a connection between two entities. It should be noted that a connection between two entities does not necessarily mean a direct, unimpeded connection, as a variety of other entities may reside between the two entities. Consequently, a connection does not necessarily mean a direct, unimpeded connection unless otherwise noted.

The general purpose of the present disclosure, which will be described subsequently in greater detail, is to provide an improved system and method for characterizing protein and nucleic acid content of single vesicles. This disclosure will focus on the application of extracellular vesicles or exosomes although the disclosed concept could also be applied to the analysis of micro or nanosized particles in general, such as liposomes, lipid nanoparticles, enveloped viruses, etc, to name a few. This concept can also be applied to single cells, but solves several problems mentioned earlier that are unique to single vesicle sequencing. Exosomes are a specific subset of EVs that are characterized by the specific cell pathway in which they are emitted. As used herein the term "extracellular vesicles" ("EV") may be used interchangeably with the term "exosomes", "microvesicles", "ectosomes", or "nanovesicles".

Extracellular vesicles (EVs) are a class of membrane bound organelles secreted by various cell types. By "extracellular vesicle" as provided herein is meant a cell-derived vesicle having a membrane that surrounds and encloses a central internal space. Membranes of EVs can be composed of a lipid bi-layer having an external surface and an internal surface bounding an enclosed volume. As described further below, such membranes can have one or more types of cargo, such as proteins, embedded therein. EVs include all membrane-bound vesicles that have a cross-sectional diameter smaller than the cell from which they are secreted. EVs can have a longest dimension, such as a longest cross-sectional dimension, such as a cross-sectional diameter ranging from 10 nm to 1000 nm, such as 20 nm to 1000 nm, such as 30 nm to 1000 nm, such as 10 to 100 nm, such as 20 to 100 nm, such as 30 to 100 nm, such as 40 to 100 nm, such as 10 to 200 nm, such as 20 to 200 nm, such as 30 to 200 nm, such as 40 to 200 nm, such as 10 to 120 nm, such as 20 to 120 nm, such as 30 to 120 nm, such as 40 to 120 nm, such as 10 to 300 nm, such as 20 to 300 nm, such as 30 to 300 nm, such as 40 to 300 nm, such as 50 to 1000 nm, such as 500 to 2000 nm, such as 100 to 500 nm, such as 500 to 1000 nm and such as 40 nm to 500 nm, each range inclusive.

The term "membrane" as used in the subject disclosure, refers to a boundary layer separating an interior vesicle space from an exterior space, wherein the layer includes one or more biological molecules such as lipids, and in some instances, carbohydrates and/or polypeptides. Membranes can include lipids and/or fatty acids. Such lipids can include phospholipids, phosphatidylserine, sphingolipids, sterols, glycolipids, fatty acids, cholesterols, and/or phosphoglycerides. Membranes can also include one or more polypeptide and/or polysaccharide, e.g., glycan.

EVs include (i) extravesicles: 30-150 nanometer diameter membraneous vesicles of endocytic origin (ii) ectosomes (also referred to as shedding microvesicles, SMVs): large membranous vesicles (ranging, for example, from 50 nm to 5000 nm in diameter) that are shed directly from the cellular plasma membrane and (iii) apoptotic blebs (ranging, for example, from 50 nm to 5000 nm in diameter): released by dying cells.

EVs, particularly exosomes, are important for intercellular communications within the human body and involved in many pathophysiological conditions such as cancer or neurodegenerative disease. EVs are abundant in various patient biological samples, e.g., biological fluids, including but not limited to blood, urine, saliva, cerebrospinal fluid, breast milk, synovial, amniotic, and lymph fluids.

In various aspects, EVs include cell fragments. In certain embodiments, EVs are produced and released by producer donor cells. The term "producer cell," as used herein, refers to a cell that releases an EVf which can be extracted or isolated from the cell culture. Producer cells are cells which act as a source for one or more EVs. Producer cells can share one or more component, such as a nucleic acid molecule, lipid, protein, lipid, and/or sugar component with derivative EVs. Producer cells can also be isolated and/or cultured cells. Producer cells can, in some aspects be modified or synthetic cells. Producer cells can be immune cells. In various instances a producer cell is a primary cell or a cell line.

As used in the subject disclosure, the terms "extracted," "extracting," "isolate," "isolated," "isolating," "purify," "purified," and "purifying," refer to a stage of a preparation of desired subject EVs, that have been subjected to one or more purification process, such as an enrichment and/or selection of the desired EV preparation. Also, a preparation of EVs can be a plurality of unknown or known amount and/or concentration. In various instances, purifying or isolating is the process of removing, such as partially removing or substantially removing, a portion (e.g. a fraction) of the EVs from a sample containing one or more biological components, such as producer cells. In various aspects, an EV composition that has been isolated is enriched as compared to the starting fraction, e.g., producer cell preparations), from which the EV composition is obtained. Such enrichment can, for example, be enrichment by 5%, 10%, 20%, 30%, 40%, 50%, 60%, 70%, 80%, 90%, 95%, 96%, 97%, 98%, 98.5%, 99%, 99.5%, 99.9%, 99.99%, 99.999%, 99.9999%, or 99.9999% or greater, as compared to the starting fraction. In some instances, an isolated EV sample has an amount and/or concentration of desired EVs at or above an acceptable concentration and/or amount. According to some versions, isolated EV preparations are free or substantially free of residual biological products. In some aspects, isolated EV preparations are 100% free, 99.5% free, 99% free, 98.5% free, 98% free, 97% free, 96% free, or 95% free, or 90% or greater free, of any contaminating biological matter such as producer cells. Undesired residual biological aspects can include unwanted nucleic acids, proteins, lipids, and/or or metabolites or abiotic materials such as including chemicals. The phrase substantially free of residual biological products can also mean that the EV composition contains no producer cells that are detectable and that only EVs in the composition are detectable. An isolated EV composition in various aspects, has no undesired activity that is detectable or, the level or amount of the detected undesired activity is at or below an acceptable level.

Also, the phrases "nucleic acid molecule," and "nucleic acid" as used herein refer to a double or single-stranded polymer of ribonucleotide or deoxyribonucleotide bases. A nucleic acid can be recombinant and peptides, e.g., exogenous polypeptides, that can be expressed when the nucleic acid is introduced into a cell. Nucleic acids can, for example, include vectors, messenger RNA (mRNA), single stranded RNA that is complementary to an mRNA (antisense RNA), microRNA (mi RNA), tRNA, small interfering RNA (siRNA), small or short hairpin RNA (shRNA), long non-coding RNA (lncRNA), chromosomal DNA, e.g., double stranded DNA (dsDNA), and/or self-replicating plasmids.

EVs can also be derived from cells by manipulation, such as indirect or direct manipulation, e.g., by extrusion or application of alkaline solutions. EVs can include organelles separated into vesicles, and vesicles produced by living cells such as by fusion of a late endosome with the plasma membrane or direct plasma membrane budding. Furthermore, EVs can be derived from a dead or living organism, cultured cells, explanted tissues or organs, or any combination thereof.

In various aspects, EVs include a cargo including, for example, a receiver, or a targeting moiety for binding to a target. A "receiver," as used herein, refers to a molecule that promotes the interaction, e.g., binding, of an EV with a target, and/or directs an EV to a target. In certain embodiments, a receiver can be a polypeptide, peptide and/or an antibody. The receiver may be naturally produced via the producer cell releasing the EV, and certain processes can be used to induce presentation of certain receivers on the surface of an EV, such as cell transfection-based methods using plasmid constructs. As used herein, a "target" is a cell, a pathogen, a metabolite, a polypeptide complex, or any molecule or structure that resides in a tissue or circulates in the circulatory system or lymphatic system of the subject, such as an immune cell or a cancer cell. A target can be any of such aspects which readily interacts with, e.g., binds, a receiver.

EVs can also include a payload, e.g. a therapeutic agent, a sugar, e.g. a glycan, simple sugar, polysaccharide, a polynucleotide, e.g. a nucleic acid, DNA and/or RNA, other molecules, or any combination thereof. The term "payload" as applied herein refers to an agent, e.g., a therapeutic agent, that acts on a target, such as a cell, that is contacted with, encapsulated by, and/or bound to an EV. In some embodiments, the payload may be naturally produced by cells that then emit the EVs with the payload. In some embodiments, the payload is not packaged by the cell into the EV; the payload may be packaged into the EVs, after EV production by cells, using methods such as electroporeation or incubation. Further examples of payloads include amino acids such as amino acids having a detectable moiety or a toxin or that disrupt translation, polypeptides such as enzymes, nucleotides having a detectable moiety or a toxin or that disrupt transcription, nucleic acids that encode a polypeptide such as an enzyme, or RNA molecules that have regulatory function such as dsDNA, miRNA, siRNA, and lncRNA, small molecules such as small molecule toxins and drugs, lipids, and/or carbohydrates.

Also, as referred to in the subject disclosure, "therapeutic molecules," or "therapeutic agents," which are also referred to as "therapeutics," are molecules or compounds that when present in an effective amount, produce a desired therapeutic effect on a subject in need thereof. Such an effect can be physiologic and/or pharmacologic. Therapeutics include one or more compounds, for example, a small molecule drug, or a biologic, such as a polypeptide drug or a nucleic acid drug, that when administered to a subject has a conveyable and/or measurable effect on the subject. Such an effect can be that it treats, such as decreases or alleviates, one or more symptom of a condition, disease, or disorder.

EVs as provided herein include exosomes. By "exosome" is meant a cell-derived vesicle composed of a membrane enclosing an internal space, wherein the vesicle is generated from a cell by fusion of the late endosome with the plasma membrane or by direct plasma membrane budding, and wherein the vesicle has a longest dimension, such as a longest cross-sectional dimension, such as a cross-sectional diameter, ranging for example, from 10 nm to 150 nm, such as 20 nm to 150 nm, such as 20 nm to 130 nm, such as 20 nm to 120 nm, such as 20 to 100 nm, such as 40 to 130 nm, such as 30 to 150 nm, such as 40 to 150 nm, or from 30 nm to 200 nm, such as 30 to 100 nm, such as 30 nm to 150 nm, such as 40 nm to 120 nm, such as 40 to 150 nm, such as 40 to 200 nm, such as 50 to 150 nm, such as 50 to 200 nm, such as 50 to 100 nm, or from 10 to 400 nm, such as 10 to 250 nm, such as 50 to 250 nm, such as 100 to 250 nm, such as 200 to 250 nm, such as 10 to 300 nm, such as 50 to 400 nm, such as 100 to 400 nm, such as 200 to 400 nm, each range inclusive. As used herein, "inclusive" refers to a provided range including each of the listed numbers. Unless noted otherwise herein, all provided ranges are inclusive.

Exosomes can be derived from a producer cell, and/or isolated from the producer cell based on one or more exosome isolating characteristics, such as density, size, biochemical parameters, or any combination thereof. In various embodiments, exosome generation does not destroy the exosome-producing cell. Exosomes can include lipids or fatty acids and polypeptides. In various aspects, exosomes include a cargo including, for example, a receiver, e.g. a targeting moiety, a payload, e.g. a therapeutic agent, a sugar, e.g. a glycan, simple sugar, polysaccharide, a polynucleotide, e.g. a nucleic acid, DNA and/or RNA, and/or other molecules, or any combination thereof. In some embodiments, EVs such as exosomes are free of and do not include genetic material such as nucleic acids therein.

As used herein, an "extracellular vesicle" or "EV" are used interchangeably and are defined to mean secreted membrane-enclosed vesicles, which include exosomes, ectosomes, microvesicles, microparticles, apoptotic bodies, and other subsets. Microvesicles, microparticles, or ectosomes are vesicles assembled at and released from the plasma membrane. They may be formed through the outward budding and fission from plasma membranes. Apoptotic bodies are derived from cells having undergone apoptosis and may contain organelles. They are generally over 1 um in size. EVs are a cell-derived vesicle having a membrane that surrounds and encloses a central space. Membranes of EVs can be composed of a lipid bi-layer having an external surface and internal surface bounding an enclosed volume. Such membranes, can have one or more types of cargo, such as proteins or RNA, embedded therein. In some embodiments, cell lines can be transfected with a plasmid or EVs can be post-modified so that the EV membranes are embedded with non-naturally occurring types of cargo such as peptides, sugars or proteins not normally embedded in the membrane of the EVs. EVs include all membrane-bound vesicles that have a cross-sectional diameter smaller than the cell from which they are derived. EVs can have a longest dimension, such as a cross-sectional diameter ranging from 10 nm to 1000 nm, such as 20 nm to 1000 nm, such as 30 nm to 1000 nm, such as 10 nm to 100 nm, such as 20 nm to 100 nm, such as 30 nm to 100 nm, such as 40 nm to 100 nm, such as 10 nm to 200 nm, such as 20 nm to 200 nm, such as 30 nm to 200 nm, such as 40 nm to 200 nm, such as 10 nm to 120 nm, such as 20 nm to 120 nm, such as 30 nm to 120 nm, such as 40 nm to 120 nm, such as 10 nm to 300 nm, such as 20 nm to 300 nm, such as 30 nm to 300 nm, such as 40 nm to 300 nm, such as 50 nm to 1000 nm, such as 500 nm to 2000 nm, such as 100 nm to 500 nm, such as 500 nm to 1000 nm, and such as 40 nm to 500 nm, each range inclusive. Cell manipulation for vesicle production can include application of alkaline solutions, serial extrusion, sonication, or any combinations thereof. In various aspects, production of a vesicle results in destruction of the producer cell. Vesicles can be derived from a producer cell, and/or isolated from the producer cell based on one or more vesicle isolating characteristics, such as density, size, biochemical parameters, or any combination thereof. In some aspects, concentrations of vesicles are free or substantially free of EVs that are derived from producer cells by fusion of a late endosome with the plasma membrane or by budding directly from the plasma membrane. Vesicles can include lipids or fatty acids and polypeptides. In various aspects, vesicles include a cargo including, for example, receiver, e.g. a targeting moiety, a payload, e.g. a therapeutic agent, a sugar, e.g. a glycan, simple sugar, polysaccharide, a polynucleotide, e.g. a nucleic acid, DNA and/or RNA, and/or other molecules, or any combination thereof.

As used herein, an "exosome" is defined to mean a secreted membrane-enclosed vesicle that originates from the endosome compartment in cells. The endosome compartment, or the multi-vesicular body, can be exocytized from the cell, with ensuing release to the extracellular space of their vesicles as exosomes. Exosomes arise as small vesicles within larger membrane structures in the endosome within a cell and have a smaller size, ranging from 10 nm to 120 nm, such as 20 nm to 120 nm, such as 30 nm to 120 nm, such as 40 nm to 120 nm, such as 10 nm to 150 nm, such as 20 nm to 150 nm, such as 30 nm to 150 nm, such as 40 nm to 150 nm, such as 10 nm to 200 nm, such as 20 nm to 200 nm, such as 30 nm to 200 nm, such as 40 nm to 200 nm, such as 10 nm to 300 nm, such as 20 nm to 300 nm, such as 30 nm to 300 nm, and such as 40 nm to 300 nm. It has been demonstrated that almost all living cells can secrete exosomes, and exosomes widely exist in various body fluids such as blood, urine, breast milk, or cerebrospinal fluid. Exosomes can carry protein, mRNA, miRNA, tRNA, yRNA, lincRNA, circular RNA, DNA, lipids, and other ingredients derived from the derived cells, and protect them from degradation by the external environment, and are beneficial to their biological function of active ingredients. Simultaneous multiplexed measurement of surface proteins and nucleic acids on single extracellular vesicles (EV). Unique DNA tags corresponding to different surface proteins and EV RNA fragments (consisting of any combination or single instance of type of RNA, such as mRNAs or microRNAs) and/or EV DNA fragments will be analyzed by next-generation sequencing. The described systems and methods may be applied to both human bio-fluid samples, non-human bio-fluid samples, and cell culture samples.

Exosomes are released from the cells when a multivesicular endosomes (MVE) fuse with the cytoplasmic membrane to release their vesicle content from the cells instead of merging with a lysosome for degradation.

Researchers have shown that various subpopulations of EVss target tissues differently. EV subpopulations are differentiated by one of many properties; such as their cell of origin, their surface proteins, or their size. The ability for EVs to selectively target tissues is likely largely mediated by the accessible surface proteins with which a receiving cell can interact to either accept, ingest and process; or reject and return to circulation. Because of the small size, sheer number and great heterogeneity of EVs they have been difficult to characterize. The described systems and methods address this issue with increased sensitivity and multiplexing capability, thereby enabling the identification of EV subpopulations and their cargo for potential targeted therapeutics.

Other objects and advantages of the present apparatus, systems, and methods will become obvious to the reader and it is intended that these objects and advantages are within the scope of the present disclosure.

To the accomplishment of the above and related objects, the disclosed apparatus, systems and methods may be embodied in the form illustrated in the accompanying drawings, attention being called to the fact, however, that the drawings are illustrative only, and that changes may be made in the specific construction illustrated.

Turning now descriptively to the drawings, in which similar reference characters denote similar elements throughout the several views, the attached figures illustrate systems and methods for characterizing protein and nucleic acid content of single vesicles without barcodes. Several iterations or possible implementations of the technology are provided in the following figures. The figures assume that the EVs have already been isolated. The addition of EV isolation to the disclosed single droplet workflow is a novel embodiment.

Figure 3A:
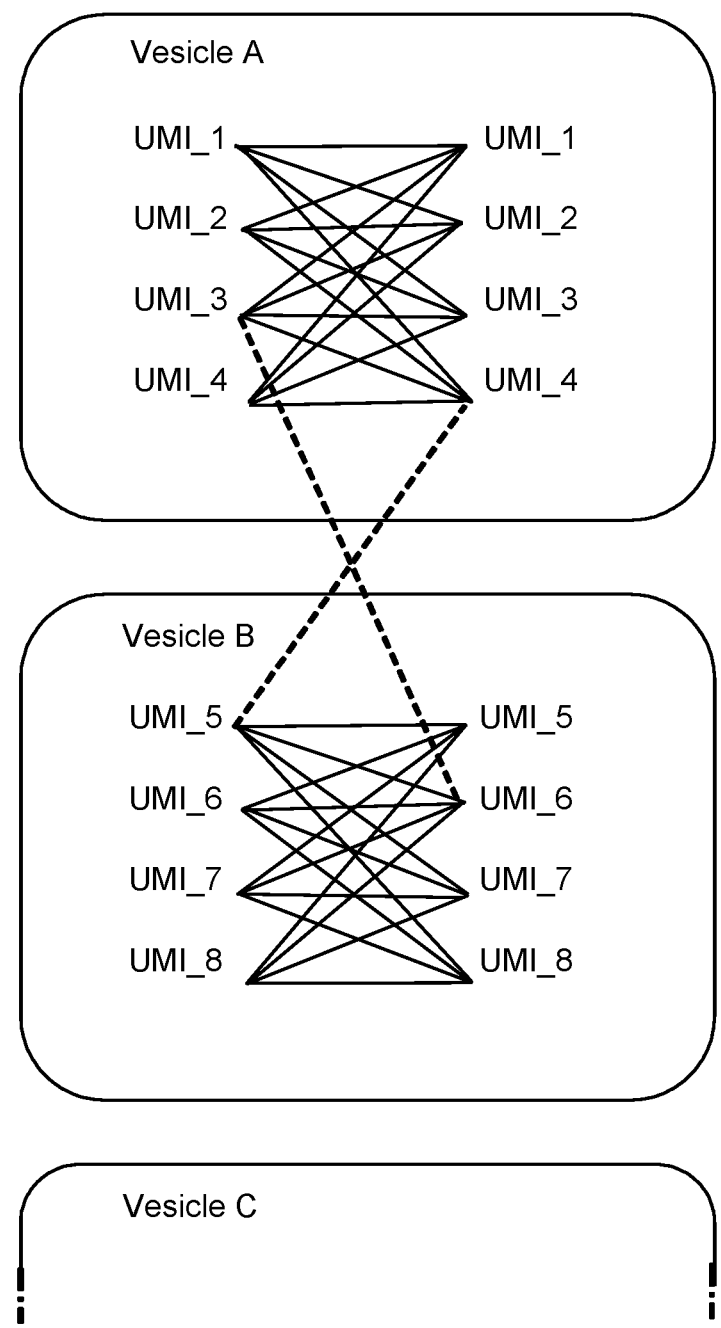
Figure 4:
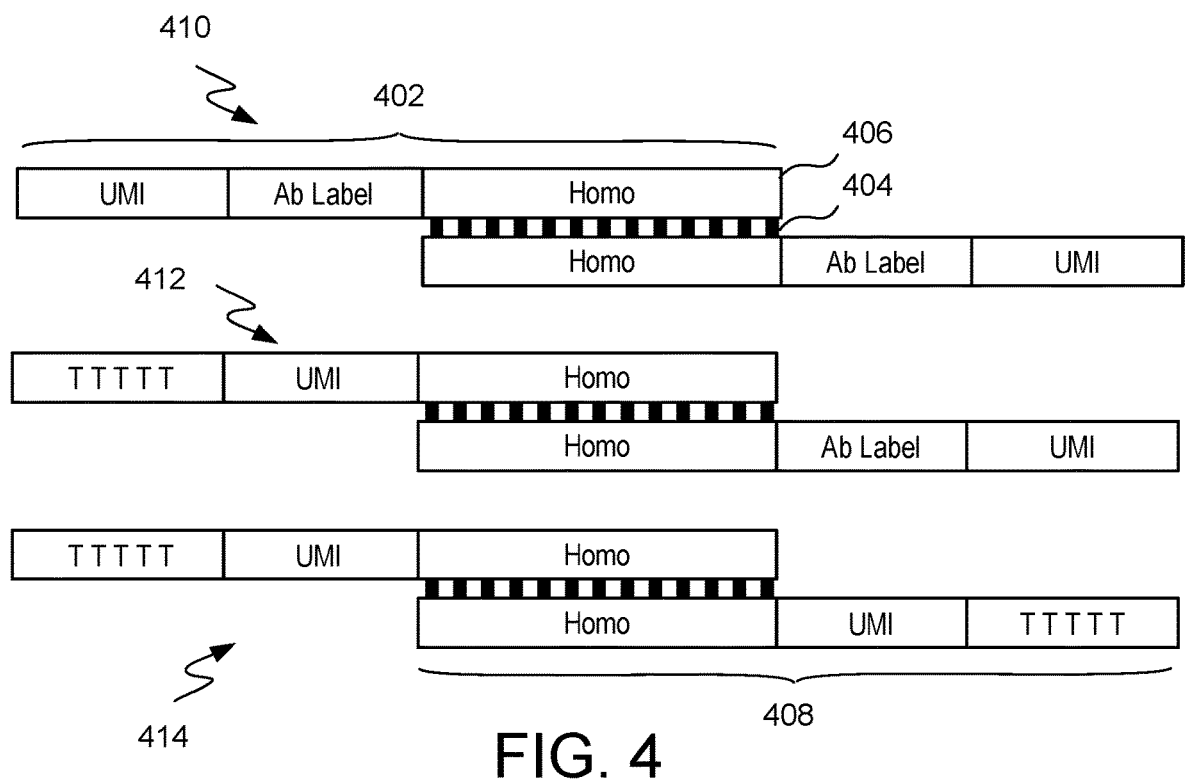
FIG. 4 illustrates example molecules essential for accomplishing methods described in the disclosure, in accordance with one or more embodiments.
Figure 5:
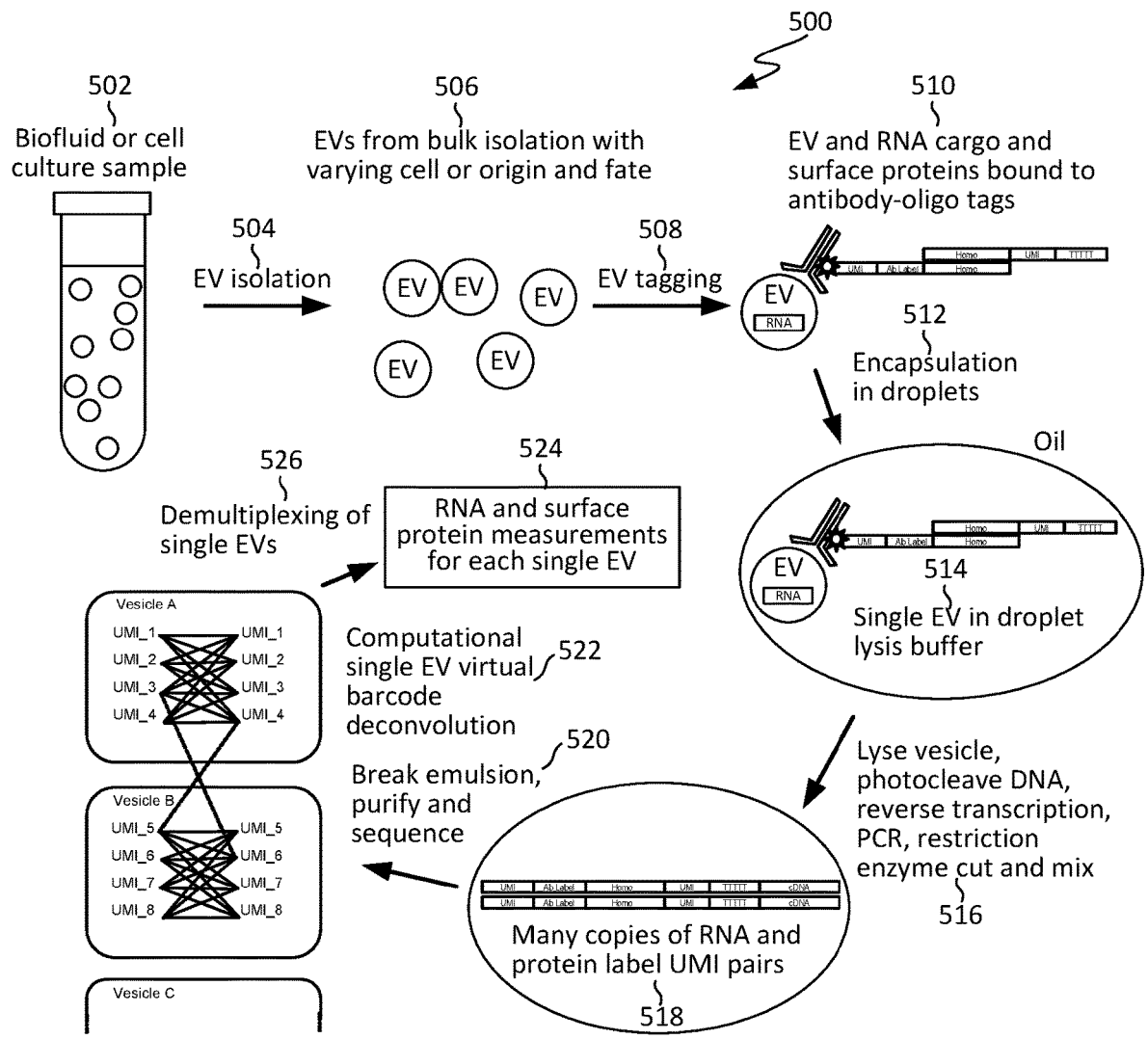
FIG. 5 Illustrates the entire systems workflow described throughout this disclosure.

According to various embodiments of the present disclosure, FIGS. 1A-1E illustrate flow process for antibody labeling, in accordance with one or more embodiments. FIGS. 2A-2F illustrate a flow process for RNA and antibody labeling, in accordance with one or more embodiments. FIGS. 3A-3B illustrate an example of barcode-free single vesicle content reconstruction, in accordance with one or more embodiments. FIG. 4 illustrates an example molecule essential for accomplishing methods described in the disclosure, in accordance with one or more embodiments. FIG. 5 illustrates the entire multiplexed single EV surface protein and RNA capture workflow. This workflow incorporates EV isolation (504), from example bulk isolation techniques (506), EVsurface protein antibody-oligo tags) linked the antibody tags with RNA fragment tags (510), thus creating unique molecular identifier (UMI) pairs, amplification (516), mixing of different UMIs to create many UMI-UMI pairs within each droplet (518) and virtually isolation of EVs (526) by clustering UMI tags belonging to the same single EV (522).

The following chart provides a direct comparison between barcode single cell sequencing, barcode with antibody sequencing, and an example method of the present disclosure.

| | Barcode method (the standard method without antibody labels) | Barcode with AbTag method (when DNA-antibody tags are used to measure proteins) | Method disclosed herein (one example method) |
|---|---|---|---|
| Collect and isolate exosomes | A. Exosomes or cells or vesicles can be harvested from cell culture, or any body fluid, e.g., blood. In certain embodiments, the exosomes can be collected using polymer-based precipitation methods, size exclusion chromatography, ultrafiltration, ultracentrifugation, immunoaffinity method, or a combination of any of the named methods. | Same as A. | Same as A. |
| Create the DNA-tagged Antibodies | Not done. | B. A selection of DNA-conjugated antibodies may be prepared to label the surface proteins on the exosomes using immunoaffinity (antibody-antigen binding). The | Same as method B, though a customized UMI and common homology domain will be designed into the nucleotide sequence which are specialized for this method. In certain |

| | Barcode method (the standard method without antibody labels) | Barcode with AbTag method (when DNA-antibody tags are used to measure proteins) | Method disclosed herein (one example method) |
|---|---|---|---|
| | | process of creating the DNA-tagged antibodies consists of several steps and includes techniques to confirm that each step was successful. The tags typically contain a way to remove the oligonucleotide from the antibody, such as containing a photocleavable linker to allow DNA release after exposure to ultraviolet light. | embodiments, if the intravesicular RNA or DNA is to be sequenced, these tags may include poly-T tails to bind to the RNA With the barcode methods these additional tags are not needed since the RNA attaches to poly-T tails on the barcodes. |
| Create the nucleotide barcodes | C. Barcodes can be manufactured in a few different ways. Barcoded beads or hydrogels can be made by repeatedly pooling, splitting, and adding a single monomer to each fraction - after just 12 repeated cycles, over 16 million unique barcoded beads can be created in this way. An alternate method is to make a barcode emulsion on a microfluidic chip by first taking a solution of single stranded DNA of random 10-mer sequences, mixing with PCR reagents and primers, and injecting through a droplet maker. The droplets are then thermocycled to amplify the single-molecule templates into a clonal population. | Same as C. | Not needed. |
| Immunoprobe the target vesicles with DNA-tagged antibodies and wash. | Not done. | D. This step is to label the surface proteins (or possibly the intravesicular proteins) using immunoaffinity (antibody-antigen binding). The purified exosomes of interest are incubated with the cocktail of DNA-conjugated antibodies. The antibodies will bind to the target proteins on the exosomes. Remove unbound DNA-conjugated antibodies - can be done with a polymer-based exosome precipitation, size exclusion column, tangential flow diafiltration or affinity separation method, for example. | Same as D although the DNA-tagged antibodies can include the site for RNA capture |
| Emulsify into droplets | E. AA commercially available droplet generator (i.e., BioRad system) or home made microfluidic droplet generating device can be used to emulsify into droplets. | Same as E | In some embodiments, same as E. In some embodiments, can be accomplished in a less precise way, such as just vigorous shaking. |

-continued

|  | Barcode method (the standard method without antibody labels) | Barcode with AbTag method (when DNA-antibody tags are used to measure proteins) | Method disclosed herein (one example method) |
| --- | --- | --- | --- |
| Merge barcode droplets with single vesicle droplets | F. Using a commercially available or home made microfluidic droplet merging device | Same as F | Not needed. |
| Merge droplets with PCR reagents | G. In some embodiments, can be included in above droplets (E), or accomplished using a commercially available or home made microfluidic droplet merging device | Same as G. | Same as G. |
| Optionally: settle into microwells | H. Using microwells can allow easier subsequent process steps. | Same as H. | Same as H. Since it is difficult to fabricate extremely large numbers of microwells, an advantage of the method described here method is the fact that it requires fewer droplets and therefore fewer comparments. |
| Free labels from their antibodies | Not done. | I. In some embodiments, the DNA-tags can be released from the antibodies, such as by using light (e.g., >300 nm UV light which does not harm DNA or RNA) to cleave a photocleavable linker. | Same as I. |
| In-droplet vesicle lysis | J. Vesicle lysis is achieved in one of many possibe ways. For example, a new line of buffer containing exosome lysis reagents is injected to each droplet. Or by incubating at 55° C. to activate proteinase K which was added in a previous step. | Same as J, but optional only if intravesicular nucleotides or other tagged payloads or tags want to be accessed. | Same as J, but optional, only needed if intravesicular nucleotides or other tagged payloads or tags want to be accessed. |
| Antibody DNA-tags attach to probes | Not done. | The released DNA-tags are then ligated or hybridized to the barcodes. | DNA-tags from antibodies and nucleotides hybridize on common homology domain. |
| Intravesicular RNA attaches to probes | Hybridizes or ligates to barcodes. Can be accomplished via simple temperature based annealing or active ligation by enzymes or amplification. | Hybridizes or ligates to barcodes. | Free intravesicular RNA binds to poly-T tail on DNA-nucleotides-tag. In certain embodiments, this method can also be modified to capture DNA cargo from the EVs. |
| In-droplet cDNA synthesis |  | After binding of exosomal RNA on the barcoded beads (either through the DNA-tag or not), the existing reverse transcriptase in the droplet will start the first strand cDNA synthesis at designated temperature. |  |
| Overlap extension amplification | Not typically done. | K. In some embodiments, this step is completed. Reagents to perform reverse transcription (such as reverse transcriptase for transcribing RNA into cDNA) can be included when droplets are formed or merged later. | Same as K |
| Restriction enzyme cut and mix | Not done. | Not done. | This is an important part of the method. When the reaction is complete, enzyme can be deactivated with heat. Thus the singlets will then re-ligate to another pair within the same droplet |

-continued

|  | Barcode method (the standard method without antibody labels) | Barcode with AbTag method (when DNA-antibody tags are used to measure proteins) | Method disclosed herein (one example method) |
|---|---|---|---|
| Break emulsion | L. Since all the information was encoded within each beads, the droplet can be broken now and the samples can be pooled for bulk analysis. Droplets are easily broken demulsifiers, like perfluorooctanol and chloroform or other methods such as electrostatic pulses. | Same as L. | Same as L. |
| Purification | M. Column DNA purification | Same as M. | Same as M. |
| Cleanup |  | Can be processed with an ssDNA-specific DNase to remove unlinked antibody barcodes |  |
| Additional amplification | N. A second round of PCR to yield sufficient DNA for sequencing | Same as N. | Same as N. |
| Creation of library | O. Follow commercially available kits and protocols | Same as O. | Same as O. |
| Sequencing and readout | P. Standard single-read or paired-end | Same as P. | In certain embodiments, paired-end sequencing js an efficient way to sequence from both ends of the strand, but many sequencing methods and library types would also work. |
| Algorithmic identification of coencapsulated (e.g. derived from the same single EV) surface cargo and internal payloads | Not done. | Not done | In certain embodiments, this is a key step. In certain embodiments, statistical or machine learning methods such as network detection or graphical models are used to infer which EV surface protein tags and which internal EV cargo tags belong to the same original EV in a droplet. |

One advantage in these disclosed methods is that they can measure RNA and protein attached to a single EV without requiring actual physical isolation of single EVs during the sample prep phase (FIG. 5, step 504), before inputting EVs into droplets. What truly matters is that we can measure the RNA and protein belonging to single EVs. The only physical isolation step required is any type of bulk isolation step, such as size exclusion chromatography or ultracentrifugation (UC). The disclosed methods takes this bulk EV isolation, containing all EVs from a biofluid sample, and then 1) differentiates true single EVs from background noise and sample contamination and 2) clusters RNAs and proteins belonging to the same single EV.

The methods and systems disclosed robustly identify true EV signals by requiring characteristic EV proteins such as CD63 and CD81 to be present along with the RNA inside a droplet. The techniques of the present disclosure can be adapted to use any specific proteins for which antibodies are available, providing the flexibility to incorporate EV proteins as defined by disease or subclasses of vesicles, such exosomes versus microvesicles. The methods can use a cocktail of proteins to ensure vesicles with different surface proteins will be captured. The system described is then able to "virtually isolate" single EV protein and RNA signal by using Unique Molecular Identifiers (UMI) on oligonucleotide labels co-encapsulated with single vesicles: it computationally clusters UMI pairs to reconstruct the contents of a single EV. The antibodies and/or RNA sequences associated to a particular vesicle are de-convolved based on which UMI pairs are more commonly associated which each other. With this process there is no need to overlap two Poisson distributions, and no need for barcodes. UMIs also enable more precise quantification of extremely small amounts of RNA such as that in EVs.

In some embodiments, the UMI clustering step involves an adjacency matrix where the columns are protein UMIs and the rows are RNA UMIs. Clustering of this matrix identifies protein UMI-RNA UMI pairs that occur more frequently than by chance, creating network hubs. Each hub is an EV constituted from protein and RNA measurements. Such algorithmic methods to deconvolve each EV hub, termed a "community", are highly scalable.

In some embodiments, an antibody DNA-tag includes a unique molecular identifier (UMI) region, perhaps from 8 to 100 base pairs long; this sequence is unique to the particular tag molecule. The DNA-tag also includes a unique sequence identifying the individual antibodies (Ab label), perhaps 8 to 100 base pairs long. This sequence is the same across all nucleotide tags for a single antibody, but different between different antibodies. The DNA-tag may also include a common homology domain, which is a specific sequence used to bind and amplify pairs of tags. This sequence is perhaps 8 to 100 base pairs long and can either be symmetric or be half one sequence and half a complementary sequence.

In some embodiments, an oligonucleotide DNA-tag includes: an RNA or DNA binding region (in the case of an RNA target this would be a poly-T tail (TTTTT) for hybridization), a unique molecular identifier (UMI) region, perhaps from 8 to 100 base pairs long (this sequence is unique to the particular tag molecule), and a common homology domain, which is a specific sequence needed to bind and amplify pairs of tags. This sequence is perhaps 8 to 100 base pairs long and can either be symmetric or the solution can be comprised of tags with half one sequence and half a complementary sequence.

In some embodiments, the order of the domains on both described DNA-tags is not critical. In some embodiments, it is important to have the common homology domain on one end, and the RNA or DNA binding domain on the opposite end, e.g. for binding availability An example of a sample preparation is provided below.

Exosome Collection

In some embodiments, exosomes can be harvested from cell culture, or any body fluid, e.g., blood. In some embodiments, the exosomes can be collected using polymer-based precipitation methods, sucrose-density gradient, flotation gradient, size exclusion chromatography, ultrafiltration, ultracentrifugation, immunoaffinity purification, microfluidic isolation or a combination of any of the named methods. The contaminants (e.g., immunoglobin proteins in the serum or proteins from the cell culture media) from the fluid sample are mostly removed during the exosome collection process. In order to further remove the exosome-free RNA from the fluid, the fluid from cell culture or any body fluid can be treated with RNAse to remove all the exosome-free RNA. After treating with the RNAse, it is important to inactivate the RNAse in order for it not to interfere in the downstream processes of exosomal RNA isolation and detection. The RNAse can be inactivated by resuspending the isolated exosome in DEPC (Diethylpyrocarbonate)-containing PBS. Alternatively RNAse can be removed using an affinity purification column or gel filtration.

DNA-tagged Antibody Production

In some embodiments, a selection of DNA-conjugated antibodies is then prepared to label the surface proteins on the exosomes using immunoaffinity (antibody-antigen binding). The process of creating the DNA-tagged antibodies consists of the following steps and includes techniques to confirm that each step was successful.

In some embodiments, antibodies against the desired EV membrane targets are selected. Generally commercially available antibodies may be selected. The specificity of these antibodies may be confirmed prior to any following steps. Specificity confirmation can be achieved in several ways, for example fluorescence microscopy can be used to image EVs or cells which are known to express the target antigen which are immobilized on a glass slide, stained with the selected antibodies and followed by fluorescently labeled secondary antibodies.

In some embodiments, the desired oligonucleotide sequences may be manufactured and obtained from one of a wide array of suppliers. The DNA must be modified with functional chemical groups that can conjugate with the antibody. Often a photocleavable linker will be utilized so that the DNA can be easily released. Note that the photocleavable modification is commercially available on any DNA or RNA sequence. A photolabile functional group (a 10-atom linker) can be cleavable by UV light (300-350 nm) and the resulting oligonucleotide will have a 5' phosphate group that is available for subsequent ligase reaction.

In some embodiments, the oligonucleotide sequence is conjugated to the antibody. Multiple strategies exist for DNA-antibody conjugation including non-covalent strategies, such as coupling via biotin-streptavidin or covalent conjugation, for example thiol-maleimide chemistry. To confirm successful conjugation of DNA tags to the antibodies, an SDS-PAGE procedure can be performed to measure changes in molecular weight of the conjugates; a shift to higher molecular weight indicates successful conjugation.

Unique Molecular Identifier Production

In some embodiments, unique sequences can be manufactured in a few different ways. One example is to take a solution containing many copies of the original antibody label and homologous domain sequence; this solution can be repeatedly split into four parts, a single monomer is then added to each of the fractions, then the fractions are repooled. For example, after just 12 repeated such cycles, over 16 million unique sequences can be created.

FIGS. 1A-1E illustrate a flow process for antibody labeling, in accordance with one or more embodiments. The steps are described in detail below.

FIG. 1A. illustrates vesicle labeling using antibody labels. In some embodiments, immunoprobes target vesicles 100 with multiple different antibodies 120 and are each labelled with unique DNA-tags 124. The DNA tags are designed to contain the following: a unique molecular identifier (UMI) 102; a unique sequence identifying the individual antibodies (Ab label) 104; and the common homology domain 106, i.e. the specific sequence needed for the subsequent hybridization amplification (Homo).

In some embodiments, this step is to label the surface proteins on the exosomes using immunoaffinity (antibody-antigen binding). The purified EVs of interest are incubated with the cocktail of DNA-conjugated antibodies. The antibodies will bind to the target proteins on the EV surface.

In some embodiments, material not bound or contained within a vesicle is removed from the sample using one various methods, such as: size exclusion chromatography; affinity chromatography; immunomagnetic of affinity bead separation; and diafiltration, ultrafiltration, tangential flow filtration, etc.

In some embodiments, the unbound DNA-conjugated antibodies can be removed using polymer-based exosome pulldown assay or using size filtration/exclusion method. It is noted that in some embodiments, the exosome collection method here needs to be a general, unbiased method, aiming to remove the unbound DNA-conjugated antibodies and retain all of the integral vesicles.

Emulsify Into Droplets

In some embodiments, the goal is to encapsulate vesicles with droplets. This can be achieved in many ways: from as simple a process as vigorous shaking of the aqueous sample with an oil in a closed container (if a surfactant is present, large numbers of miniscule stable aqueous droplets suspended in oil are produced), to microfluidic devices which precisely form similarly sized aqueous droplets in oil solution. In one embodiment, the DNA-antibody bound vesicles and the reagents (i.e., ligase solution) are loaded in a commercially available droplet generator (i.e., BioRad system) or homemade microfluidic droplet generating device. Single vesicles and the reagents are encapsulated into one droplet. It is noted that properly diluted samples are needed to avoid two or more vesicles in the same droplet.

In some embodiments, it may be advantageous to settle individual droplets in individual microwells of the chip to simplify the downstream processes. Multiple active ways can enhance settling; such as centrifuging or a wetting mechanism. The size of the microwells can be designed to ensure single droplet/vesicle isolations. If a microwell device is used, the following steps can be performed after using a detergent-based reagent to lyse the vesicles and break the droplets on chip. Single vesicle containing droplets can be directed into individual microwells on a microfluidic chip using an acoustofluidic platform. When surface acoustic waves are applied to the device, each droplet will be pushed into the microwells inside the microchannel. Alternatively, electrowetting processes can also be applied to direct individual droplets to move on the microfluidic chip and fall into the microwells. The microwells are designed to fit single droplets. The microfluidic chip with the microwells can be fabricated using high density polyacrylamide gel against Si-mold. The high density polyacrylamide gel fabricated microwell is designed to prevent EV RNA or other internal payloads from a single vesicle to diffuse laterally and prevent contamination between neighbor vesicles. With the samples trapped in the microfluidic device, the reagents can be easily applied by pouring or pipetting or flowing directly on the chip. Additionally, the wash steps can also be easily performed by pouring or pipetting a wash solution.

Figure 1B:
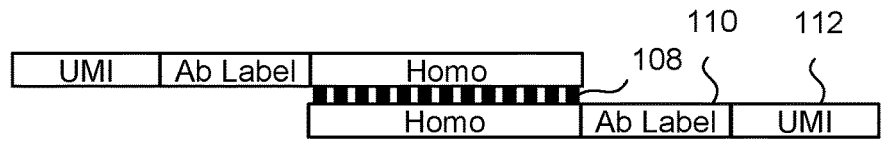

FIG. 1B illustrates freeing labels from their antibodies and allowing them to hybridize. In some embodiments, photocleavage is used to cleave DNA-tags from antibodies in the droplet. To break the DNA-tags from the antibodies, the bonds between the DNA-tag and the antibody are photo-breakable linkers 122. DNA-tags are then released from the antibodies using light (e.g., >300 nm UV light which does not harm DNA or RNA). In some embodiments, enzymes can be used to cleave enzymatic linkages between DNA-tags from antibodies in the droplet instead of light. Next, free strands are allowed to hybridize 108. In some embodiments, the buffer will also likely contain reagents to perform reverse transcription (such as reverse transcriptase for transcribing RNA into cDNA).

Figure 1C:
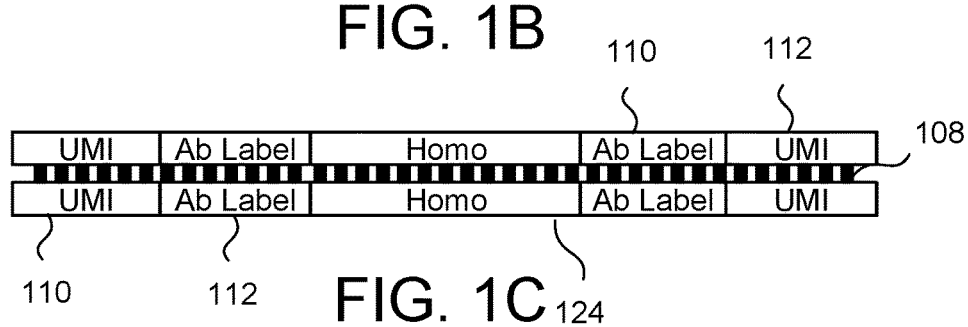

FIG. 1C. illustrates amplification of the strands. In some embodiments, Overlap Extension PCR (OE-PCR) will be used to produce products only when two strands are hybridized to each other. This method can be tested by including only nucleotide strands containing one half of the complimentary common homology domain—here no OE-PCR products should be produced. In some embodiments, when complimentary strands are present, multiple copies of each UMI paired strand 112, as well as AB label 110, will be produced while unpaired strands will not be amplified.

Figure 1D:
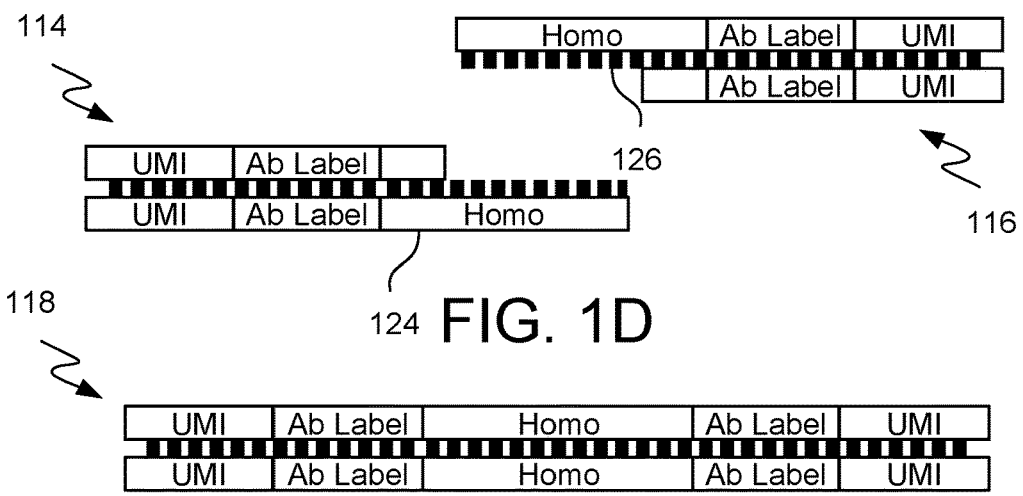

FIG. 1D. illustrates restriction enzymes cutting and mixing the strands. In some embodiments, an enzyme is added or activated at this point that will precisely cut at a section 126 of the common homology domain 124.

In some embodiments, the nucleotide strands 114 and 116 are free to mix and will not permanently recombine until the restriction enzyme is inactivated. In some embodiments, one such way to inactivate a restriction enzyme is through the precise application of heat.

Figure 1E:
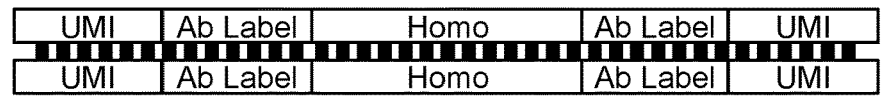

FIG. 1E. illustrates binding of the label pairs. In some embodiments, once the restriction enzyme is inactivated, strand pairs 114 and 116 can then ligate or hybridize within the droplet, forming new label pairs 118. In some embodiments, the ligase (e.g., T4 DNA ligase) used here will be responsible for binding together the label pairs 114 and 116 that were separated as shown in FIG. 1D. In some embodiments, the key here is that the individual labels will have mixed and matched so the pairs are no longer the same as they were when amplification occurred. In some embodiments, it is noted that the ligase and its solution (e.g., ATP containing buffer) may be encapsulated with the exosomes and barcoded beads from the moment of droplet creation.

FIGS. 2A-2F illustrate a flow process for RNA and antibody labeling, in accordance with one or more embodiments. The steps are described in detail below.

Figure 2A:
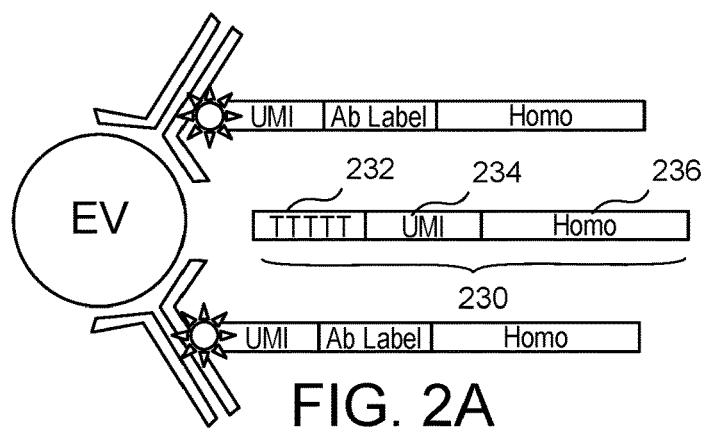
FIGS. 2A-2F illustrate a flow process for RNA and antibody labeling, in accordance with one or more embodiments.

FIG. 2A illustrates RNA and antibody vesicle label processes. FIG. 2A starts with immunoprobe target vesicles with different antibodies labelled with unique DNA-tags. This step is similar to the one described above with respect to FIG. 1A. In addition, the wash step is also similar to the one described above with respect to FIG. 1A.

In some embodiments, the RNA within target vesicles are labeled with unique DNA-tags 230. The DNA tags are designed to contain the following: poly-T tail (TTTTT) 232; unique molecular identifier (UMI) 234; and specific sequence needed for following hybridization and amplification (Homo) 236. In some embodiments, these tags are added independently from the antibody DNA-tags, in alternative embodiments the UMI and poly-T tails are already part of the antibody DNA-tag. In some embodiments, vesicles are emulsified into droplets and optionally settle into microwells in a manner similar to the one described above with respect to FIG. 1A.

In some embodiments, in-droplet vesicle lysis is required in order to release the RNA contents of the vesicle for subsequent process steps. In some embodiments, a buffer containing exosome lysis reagents (such as detergent) may be included when the droplet emulsion was created. In some embodiments, lysis could also potentially be achieved by freeze thaw cycle. In some embodiments, a detergent-based reagent may be used to lyse the vesicles after photo (or enzymatic) cleavage of the DNA-tags from antibodies. In some embodiments, a droplet containing EV lysis reagents and reverse transcription (RT) reagents can be merged with each droplet encapsulated single EV. In some embodiments, the RT-EV lysis reagent mix serves as a single buffer containing reagents to lyse the EVs (such as detergent) and reagents to perform reverse transcription (such as reverse transcriptase for transcribing RNA into cDNA). In some embodiments, RNAaseOUT recombinant ribonuclease inhibitor (e.g. a noncompetitive inhibitor of ribonucleases such as RNAse A) or other RNAse removal reagent can also be included in the buffer for reducing any chances of RNA degradation by RNAse.

Figure 2B:
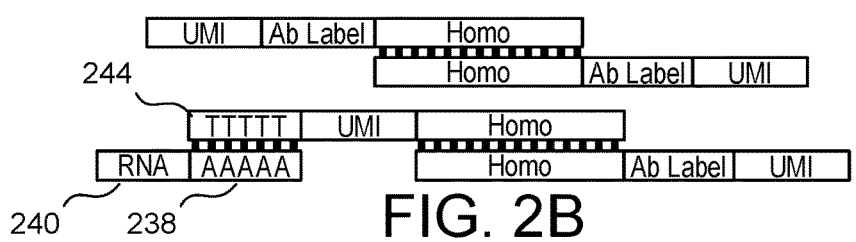

FIG. 2B. illustrates freeing labels from their antibodies and allowing them to hybridize. This step is also similar to the one described above with respect to FIG. 1B. In some embodiments, the released vesicular RNA will hybridize on the poly-T tail 244 of the Poly-T DNA label. In eukaryotes (e.g., human cells), polyadenylation is part of the process that produces mature messenger RNA (mRNA) for translation. The mRNA can be packaged into the exosomes in the human cells. Thus, a DNA sequence with poly-T-tail can be used to effectively capture mRNA in exosomes. Additionally, pre-miRNAs are transcribed by RNA polymerase II and comprise of a 5'-cap 240 and poly-A tail 238 as well. Additionally, in some embodiments, to ensure we capture the mature miRNAs which don't have poly-A-tail, polyadenylation process can be performed on the miRNAs before the hybridization process. This process/kit is commercially available. For example, ABM Inc. has miRNA-cDNA synthesis kits including poly(A) polymerase which catalyzes the template independent addition of adenosine residue onto the 3-end of polyribonucleotides. For the purposes of this example, the miRNA will be poly-A-tailed.

Figure 2C:
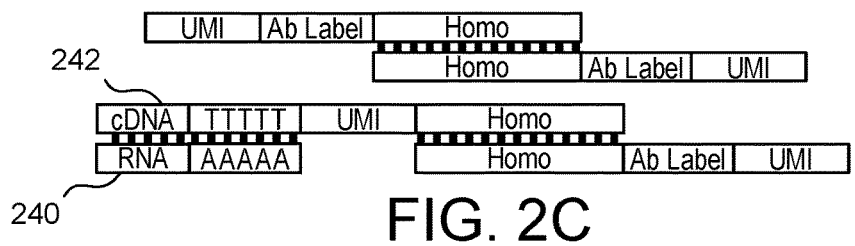

FIG. 2C. illustrates creating cDNA 242. In some embodiments, the droplet encapsulated buffer will also likely contain reagents to perform reverse transcription (such as reverse transcriptase for transcribing RNA into cDNA). The existing reverse transcriptase in the droplet will start the first strand cDNA synthesis at a designated temperature. Next, RNA 240 is removed from the cDNA 242. In some embodiments, this process is similar to stranded cDNA synthesis.

Figure 2D:
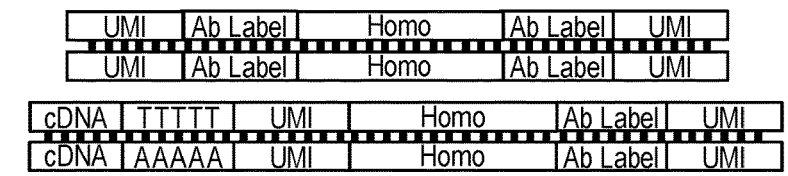
Figure 2E:
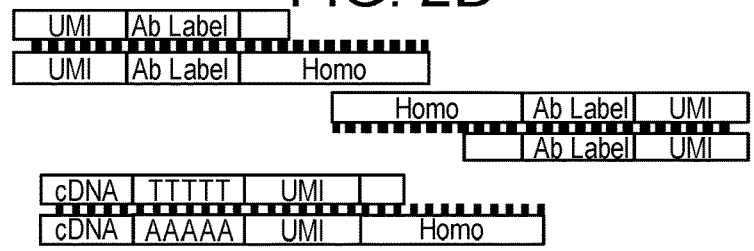
Figure 2F:
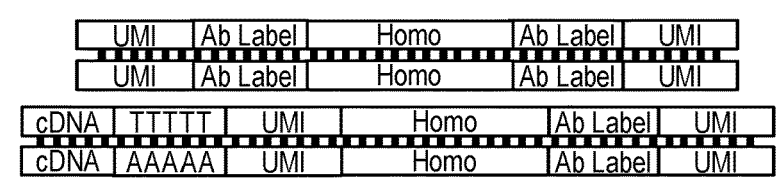

FIG. 2D. illustrates amplification, in a manner similar to the one described above with respect to FIG. 1C. FIG. 2E. illustrates restriction enzyme cutting and mixing, in a manner similar to the one described above with respect to FIG. 1D. FIG. 2F illustrates ligating within a droplet, in a manner similar to the one described above with respect to FIG. 1E.

Break Emulsion

In some embodiments, the paired UMIs contain information regarding the exosome-of-origin, although not in a totally obvious way. The antibody DNA label comprises information regarding the specific antibodies present. The UMIs will also enable quantification of copy numbers. Since all the information was encoded within each droplet, the droplet can be broken now and the samples can be pooled for bulk analysis. Droplets are easily broken using demulsifiers, such as perfluorooctanol and chloroform, or other methods, such as electrostatic pulses.

Create and Purify Library

In some embodiments, a library is created and purified. In some embodiments, this may be accomplished using commercially available kits and protocols.

Next-Generation Sequencing

In some embodiments, this step involves a fairly common paired-end sequencing methodology which allows users to sequence both ends of a strand. In this way, the two UMIs, which are physically connected on a strand, can be associated with each other in the subsequent data processing.

FIGS. 3A-3B illustrate an example of barcode-free single vesicle content reconstruction, in accordance with one or more embodiments. The details of the reconstruction are described below.

Reconstructing Single Vesicle Information Using Clustering Algorithm Based on Common Pairs In some embodiments, NGS data is analyzed using an algorithm to reconstruct which antibody labels and/or RNA sequences were contained within a droplet based on which UMI pairs are more commonly associated which each other (solid lines in schematic FIG. 3A) and which pairs are rare or nonexistent (dashed lines in schematic FIG. 3A).

In some embodiments, the UMI pairs indicate that two UMIs co-occurred. The frequency of co-occurrence of UMI pairs can be used to identify single vesicles using network-based methods. This is because the UMI pair information can be stored as a symmetric adjacency matrix (FIG. 3B), with each column and row corresponding to a specific UMI. The data inside one row, column index of this matrix is the number of times that UMI-UMI relationship occurred.

In some embodiments, UMI-UMI relationships with a high co-occurrence and high frequencies of occurrence for the different pairs are more likely to constitute a genuine vesicle. One class of network-based methods that would be appropriate to determine which UMI-UMI pairs originated from a genuine vesicle and not simply spurious noise is community detection algorithms One example of a community detection algorithm is the Girvan-Newman method; it identifies closely connected hubs of nodes, meaning the nodes contain many shared edges beyond just a single bidirectional 1:1 relationship between two nodes. In this case, the edges are bidirectional, meaning there is not a directed relationship between two UMIs. The weight of the edge is the number of times a UMI-UMI occurred and this weight is what is stored in the row, column index of the adjacency matrix.

In some embodiments, a hub of nodes, termed a "community", is a single vesicle from a single droplet in this case. The nodes are simply the coordinates from the adjacency matrix. Nodes that contained very few interconnected edges, or edges that are extremely low frequency, will be identified as very small communities. Such small communities can be identified as non-vesicles due to their low node and edge count. Communities below a certain threshold of number of nodes, number of edges, the weights of the edges, or a combination of these features, are then removed from downstream sequencing and analysis because they do not constitute true vesicles. These thresholds can be set based upon heuristics (for example, a community with only one UMI-UMI relationship that occurs once is highly unlikely to constitute a true vesicle, given that both extracellular vesicles and cells are known to generally contain several proteins on their surface) or by experimental validation. Experimental validation to determine the thresholds could be performed by comparing the number of spurious UMI-UMI relationships and their co-occurrences using negative controls, such as water or fluids known to not contain vesicles. Vesicles from a highly purified subpopulation, with a set of known, a priori surface proteins that co-occur on those vesicles, can also be used as a positive control to understand the general level of UMI-UMI co-occurrence and frequency in a real vesicle population.

In some embodiments, another algorithmic class of methods to delineate between real vesicles and spurious noise and to label UMI-UMI pairs from each vesicle is clustering, or unsupervised learning, methods. Unlike community network detection methods, the number of end clusters, or in this case true (and false) vesicle populations, must be determined using additional algorithmic methods. For example, the earlier described adjacency matrix can be clustering using a hierarchical clustering algorithm like Ward's method that produces a dendogram (tree), or a k-means clustering method like Lloyd's method that iteratively updates clusters to optimize the similarity between all objects (in this case, indices in the UMI-UMI matrix). The hierarchical methods produce a dendogram of increasingly smaller clusters, with leaves at the end having one cluster (UMI) each. The k-means method requires an automatic input of the number of clusters before even running the optimization similarity algorithm. Methods to select the number of clusters include the Silhouette method and consensus clustering. Consensus clustering resamples the adjacency matrix, and clusters for several iterations that are pre-defined (usually 100 iterations is acceptable), and then does this for a sequence of possible cluster number values. The cluster number that appears the most stable is chosen as the final cluster number. Clusters that then have a low number of UMIs, using thresholds like described above in the Girven-Newman example, are considered false positives and not real vesicles, and thus the UMI-UMI pairs assigned to these clusters are not kept for downstream analysis.

In some embodiments, single vesicle data usually brings computational constraints. Network-based methods, as opposed to clustering methods, as differentiated above, tend to be more ideal for computationally-heavy workloads with very large matrices. Indeed, because they were designed for large social network analysis, they are especially appropriate for fast computation of vesicle populations to identify genuine vesicle populations.

FIG. 4 illustrates some unique molecules 410, 412, and 414 which can be used to accomplish the methods described in the present disclosure. The molecules consist of several possible forms which all have the characteristic of comprising two of UMI sequences separated by a restriction enzyme site 404. The molecules pictured are all pairs of oligonucleotides, bonded on a common homology domain 406. Each pair consists of two antibody DNA-tags 402 (strand 410), two nucleotide DNA-tags 408 (strand 414), or one of each (strand 412).

FIG. 5. represents the entire sequential process of methods described above (500). The process 500 begins with a biofluid or cell culture sample (502), from which EVs are isolated (504). In certain embodiments, a bulk isolation method is used, such as size exclusion chromatography to isolate all EVs (506), regardless of their surface protein and lipid compositions, within a desired size range, for example, in some embodiments, from 50-200 nanometers. Then the process of EV tagging begins (508), where the antibody portions of the UMI antibody-oligo tags attach to the surface proteins of each EV, which in certain embodiments may contain RNA cargo (510). Next, EVs are encapsulated inside chambers such as aqueous droplets in a water-in-oil emulsion (512), with rarely more than a single EV per droplet. At this point the antibody-oligo tags can be photocleaved to separate the oligo tag from the antibody. In certain embodiments the EV in each droplet may be lysed using a buffer (514) to release the internal RNA of each E. Each fragment of EV-derived RNA then hybridizes to the EV-derived RNA capture portion of the oligo tags. Reverse transcription is employed to synthesize DNA from the captured RNA. Then, the DNA strands which contain UMI-UMI pairs are amplified one or more times within the droplet using PCR. The amplified pairs are cut using a restriction enzyme specific to a site between the UMIs and upon deactivation of the enzyme, the pairs randomly reconnect within each droplet (516) to create many instances of UMI replicate—UMI replicate pairs (518). The individual chamber, i.e. droplets, are now merged, such as by breaking the emulsion with a detergent, and the resulting material sequenced (520) to allow for computational deconvolution of each UMI-UMI replicate pair (522) which allows for demultiplexing to assign each pair to its original droplet (526) and thus assign EV internal RNA and EV surface proteins to their EV of origin (524).

Advantages

In some embodiments, a significant advantage of the methods and systems of the present disclosure is due to the fact that NGS read counts have a time and cost associated with them. If NGS capabilities improve to the point where reads are less precious, the technology described in the patent disclosure would not be as useful. This is unlikely.

In some embodiments, a second advantage is the potential simplicity of reagents and workflow compared to alternatives. It is conceivable that barcoded droplets could be produced in a way where a large proportion of droplets contain a single barcode and a single vesicle via sorting, active droplet forming technologies, or advanced micro-manufacturing methods, although such methods would prove challenging.

In some embodiments, another advantage of simultaneously measuring exosomal surface proteins and RNA is the discovery of de novo RNA cargo associated with particular subgroups of vesicles defined by their surface markers. This measurement capability applied to clinical human blood samples and merged with data science will enable the discovery of new targeted therapeutics. Any methods or technologies that reduce the cost and complexity of obtaining this data would be valuable. The methods described in the present disclosure are particularly advantageous due to the ability to amplify and thereby detect low abundance tags, to correct read counts using UMIs, and the ability to process large numbers of vesicles.

A technology platform that characterizes the exact regulatory messages sent between individual cancer cells through single EV measurements would be of immense value to researchers and companies developing novel diagnostic assays, drug targets, and drug delivery vehicles. This is because EVs can be measured in patient blood samples, contain RNA payloads that elucidate potential new druggable pathways, and can also be repurposed as drug delivery vehicles.

The methods disclosed in the present disclosure address several pain points highly relevant to the unique challenges of measuring single EVs. The methods disclosed herein eliminate the need for costly and time-consuming stringent EV isolation processes because it computationally eliminates noisy free-floating protein and RNA signal. The need to measure both protein and RNA in a multiplexed manner is also more pressing for single EV NGS than for single cell NGS. Common cell types are already defined using characteristic surface protein markers[10], but we are lacking such definitions of EV types, i.e. EV subpopulations. A multiplexed approach that measures both EV surface proteins and internal RNA would greatly accelerate cataloguing of novel EV subpopulation types while also providing insights into their functional cell of origin and cell fate RNA regulatory mechanisms.

The methods disclosed in this present disclosure are the first single EV NGS technology. They also embody the first technology that can computationally define cancer cell EV subpopulations beyond gross cell line or disease state. These methods will decrease per-sample sequencing costs in several ways: by eliminating the use of barcoded beads, simplifying the upfront EV isolation step, and removing EVs with no RNA cargo from downstream sequencing. The methods and ideas disclosed will also increase reproducibility of EV measurements by isolating EVs with high purity. Finally, it will provide rapid, scalable identification of proteins and RNAs belonging to the same individual EVs.

Unlike current single cell RNA-seq methods, which employ barcoded beads, the co-occurrence of Unique Molecule Identifiers (UMIs) from protein antibody and RNA oligonucleotide tags inside each EV droplet allows the methods disclosed herein to computationally group EV protein and RNA derived from the same single EV.

In addition to providing insight into very early-stage cancer as well as more advanced disease, the methods disclosed herein may improve our understanding of cancer cell communication, and offer insights into new drug targets, drug delivery vehicles, and diagnostics. These methods can be used on human, animal or bacterial fluids and cell culture samples from any type of disease. The key advantages of the new technology and methods disclosed herein include: multiplexed protein and RNA, decreasing cost and increasing yield, hours of time and money saved through simplified sample prep, reproducible isolation of single EVs with high purity from noisy samples, and rapid and scalable data output. The methods and systems disclosed herein described multiplexes protein and RNA, and they also provide orders of magnitude improvements in reagent cost and scale by eliminating the need for barcodes inside every single droplet. This is achieved through virtually isolating single EVs by computationally identifying which UMIs belong to which EV, and thus which surface proteins and internal RNAs belong to which EVs. The methods described herein also save time and money because existing EV RNA-seq methods require laborious upstream isolation processes, but the methods described herein can be "plugged" into any upstream EV isolation method and inherently refines EV isolation. A user of this technology can use any crude upstream isolation step to separate EVs from cells and let the technology handle the more nuanced step of contamination removal. This technology also quickly identifies empty droplets and avoids sequencing them because it detects which droplets contain EVs through detection of EV surface antibody tags. It is hypothesized that not all EVs contain RNA cargo; these "blank" EVs need to be removed to avoid wasted NGS reagents. Additionally, EVs must be isolated from cells and other free-floating contaminants before sort of characterization. The methods described herein elegantly performs single EV isolation in a virtual manner by constructing a network from the surface protein and internal RNA Unique Molecular Identifiers (UMI) found inside each droplet. It is critical that free-floating protein and RNA is removed from the droplet before the EV is lysed. This contaminating material is not a critical problem in single cell RNA-seq because a cell contains much more RNA and protein than an EV. With EVs, the signal to noise ratio can become distorted if contaminants are not removed. The methods disclosed herein achieve this by only quantifying RNA that is derived from EVs; it isolates only EVs via its EV surface antibody tags. Finally, the methods described herein "virtually" isolates single EVs through computational network theory. Each network hub is an EV constituted from protein and RNA measurements and the algorithms to define these hubs are highly scalable. This new technology effectively takes a physical task, assigned of proteins and RNAs to each individual EV, and turns it into a computational task, but applying network theory to the UMI antibody-oligo tags within each droplet.

Although many of the components and processes are described above in the singular for convenience, it will be appreciated by one of skill in the art that multiple components and repeated processes can also be used to practice the techniques of the present disclosure.

EXAMPLES

The following examples are put forth so as to provide those of ordinary skill in the art with a complete disclosure and description of how to make and use the present disclosure, and are not intended to limit the scope of what the inventors regard as their present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: This example simulates an expanded number of scenarios for algorithmic assignment of UMIs to individual droplets from the single embodiment example shown in FIG. 3B. This is the step in FIG. 5 referred to as the demultiplexing of single EVs. Table 1 presents the various simulation parameters used in different programmatic iterations of the simulations via a programming script.

Parameters Evaluated in the Simulations: Number of EVs Per Sample

Combinations of the parameter values in Table 1 were used to create the simulated datasets. The number of EVs is the total number of EVs in the sample. This parameter is the only parameter in the table below that is vastly downsampled from expected ranges observed in biofluid or cell culture samples; the number of EVs in 1 mL of human blood serum, for example, is approximately $1\text{-}3\times10^{12}$, and from urine, approximately $3\text{-}8\times10^{9}$ (Li, Zeringer, Barta et al. Philos Trans R Soc Lond B Biol Sci. 2014, 369(1652): 20130502). A significantly lower number of EVs was used in the simulations because this parameter is because it is the least sensitive for evaluating accuracy of the methods, and using the R computing environment, the simulations were limited by memory constraints (e.g. handling very large matrices with over 10,000 rows becomes an issue, specifically for the R computing language, not other computing languages used in other embodiments.) The number of EVs is also the number of starting droplets.

Parameters Evaluated in the Simulations: Number of RNA Fragments/EV

The number of RNA fragments/EV is the number of RNAs found inside each EV. The average number of RNA fragments per EV is still under investigation in the research community; the methods disclosed herein will help improve the exact quantification of the number of RNAs per EV. It has been estimated that the average number of miRNAs per EV ranges anywhere from approximately to 0.008 to 10 and beyond with a variance around 0.02 (Chevillet, Kang, Ruf et al. PNAS Oct. 14, 2014 111 (41) 14888-1489, Stevanato, Thanabalasundaram, Vysokov, Sinden. PLoS One. 2016; 11(1): e0146353.) Given there are multiple species of RNAs inside EVs beyond miRNAs, (Pérez-Boza, Lion, Struman. RNA 2018. 24: 423-435, Lv, Li, Zhang. Front. 2017 Microbiology. 12 June), the number of all RNAs per EV ranges from a rough approximation of 0.15 to 210. The parameters noted in the table were used as the lambda value in a random Poisson distribution; this means that it was used as both the mean and the standard deviation for the distribution. By computing a random Poisson, the R script returned a slightly different value of the number of RNAs per EV to simulate a realistic scenario where the number of RNA fragments found inside a single EV is possibly a somewhat random queue biological process as the cell packages the EVs along with internal RNA cargo. DNA cargo was not simulated in this example but would follow a very similar method for simulations; the average number of DNA per EV would simply be adjusted based on literature values, which suggest there are upwards of a 1000 copies of DNA per EV in certain biological states (Fernando, Jiang, Krzyzanowski, Ryan. PLoS One. 2017).

Parameters Evaluated in the Simulations: Number of Antibodies Attached Per EV

The number of antibodies attached per EV is the number of antibodies (attached to UMIs) that attach to the surface proteins on each EV. The number of RNAs per EV and the number of antibodies per EV sum to create the total number of UMIs per EV. Thus, in the algorithm portion of the methods disclosed, simulated in this example, it does not matter what portion of total UMIs are contributed by antibodies or by RNAs. The parameters noted in the table were used as the lambda value in a random Poisson distribution; this means that it was used as both the mean and the standard deviation for the distribution. By computing a random Poisson, the R script returned a slightly different value of the number of antibodies per EV, for each EV (i.e. droplet), to simulate a realistic scenario where the number and type of proteins on an EV is a possibly somewhat random queue biological process as the cell packages the EVs with certain proteins in their membranes (and the certain selected UMI-antibody used for capture then bind to some or all of these membrane proteins on the EVs.)

Parameters Evaluated in the Simulations: Number of Amplifications

The number of amplifications is the number of amplification cycles used in the upstream sequencing process. This effectively amounts to the number of replicates of a specific UMI that may be found inside a droplet. The number of amplifications equals the number times that UMI is in a UMI-UMI pair, in a scenario where all UMIs in a droplet are paired with another UMI. Thus, the number of amplifications is also directly related to the number of UMI-UMI edges that may be incorporated into the algorithm from a single droplet. More edges means heavier weights, which can reduce errors, presuming spurious or incorrect UMI-UMI pairings between two distinct droplets (and thus EVs) occur at a much lower rate than the amplification rate. The number of amplifications for many RNA-seq settings tends to be around 10 amplification cycles. The main limit on number of amplification cycles relates to the total number of reads a sequencer can measure in a single run. As of today, the Illumina Hiseq can sequence about 2 billion reads in one one; it is expected that sequencing technologies will continue to improve to be able to increase the number of reads sequenced per run and thus allow for increasingly larger samples of EVs, with many antibodies and RNAs per EV, at high amplification rates.

Parameters Evaluated in the Simulations: Percent of UMIs with Noise

The percent of UMIs with noise is the percent of unique UMIs that contain at least one pairing that is incorrect, i.e. is paired with a UMI from another droplet. The current sequencing error rates are below approximately 0.1% (Glenn, Molecular Ecology Resources. 2011, 15 Aug.). These simulations tested similar levels but also much higher levels to understand how the UMI-UMI pairings can help deconvolve reads into single droplet assignments in noisy sequencer scenarios.

Parameters Evaluated in the Simulations: Number of Amplified Replicates Per UMI With Noise The number of amplified replicates per UMI with noise is the number of UMI replicates, per unique UMI, that are paired with UMIs from a different droplet, and thus are incorrect UMIs. The higher this number, the higher the weight given to a UMI-UMI pair that is incorrectly assigned between two droplets, thus boosting the chance that this UMI-UMI pair may result in an assignment to an incorrect droplet. It is of note that in certain embodiments, edges with a low weight (low number of UMI-UMI pairing occurrences) may be thresholded and removed before implementing this algorithmic demultiplexing step. This will help ensure noisy reads to not get sequenced and overly biased droplet assignments. This thresholding was not completed in this simulation, in order to easily interpret the end results.

Parameters Evaluated in the Simulations: Network Detection Method

Two different network detection methods were tested: the edge betweenness (also known as the Girvan Newman method) (Girvan, Newman Proc. Natl. Acad. Sci. USA 2002, 99:7821-7826) and the Walktrap method (Pons, Latapy, Journal of Graph Algorithms and Applications. 2006, 10:2: 191-218). The two methods use different mathematical techniques, illustrating that the methods disclosed herein are not restricted to one specific algorithm implementation to demultiplex the UMI-UMI pairings and correct sort UMIs into single droplet (and thus EV) assignments. For the edge betweenness method, the edge betweenness score of an edge measures the number of shortest paths through it. The concept of edge betweenness community structure detection is that it is likely that edges connecting separate modules have high edge betweenness as all the shortest paths from one module to another must traverse through them. So if the algorithm gradually removes the edge with the highest edge betweenness score derived from a hierarchical map or rooted tree graph (i.e., a dendogram). The leafs of the tree are the individual vertices and the root of the tree represents the whole graph. Thus, the edge betweenness community detection algorithm calculates the edge betweenness of the graph, removing the edge with the highest edge betweenness score, then recalculating edge betweenness of the edges and again removing the one with the highest score until all nodes are assigned to a community, also known as a cluster, and in this case specifically, a droplet which represents a single EV. The walktrap community detection algorithm takes a different approach; it finds densely connected subgraphs, also called communities, in a graph via random walks. The idea is that short random walks tend to stay in the same community. The walktrap method in particular is highly scalable to computations much larger than the ones illustrated here. We observed that in the R computing language, the Walktrap method, as compared to the edge betweenness method, could be run without memory issues on a 2 CPU, 7.5 GB cloud server for simulation scenarios that assumed more EVs and more antibodies and/or RNAs per EVs, all of which increase the size of the adjacency matrix and the networks being computed.

Computing Environment

Multiple datasets of sequencing data after the UMI-UMI pairs are amplified and then sequenced were simulated using a programmable script using the R computing language (Version 3.4.1) on a 2 CPU, 7.5 GB cloud server. Packages used for this analysis include the 'igraph' package version 1.2.1 and the 'Matrix' package version 1.2-14. The igraph package contains methods for network detection algorithms, also known as community detection algorithms. The Matrix package was used to transform the adjacency matrix of each simulated datasets' UMI-UMI edge weights (a weight of once means UMI A and UMI B were found to be connected once, as measured by the sequencing output of a UMI A-UMI B strand) into a sparse matrix for faster computational time. The use of a sparse matrix or any specific type of matrix is not inherently required to implement the methods described in this present disclosure. Additionally, other network detection software packages, in R or other languages, can be easily substituted for the 'igraph' package here, the use of 'igraph' is only meant as a representative exemplary implementation of the methods disclosed. Additionally, methods beyond network or community detection methods can be used, such as clustering algorithms (e.g. k-means or hierarchical clustering), vector quantization, graphical models or deep learning methods. Often, mathematically, such methods share similarities; for example, the edge betweenness, or Girvan-Newman community detection method implemented in this example, creates an output of droplet assignments (communities) for UMIs that can be interpreted as a dendogram, which could then be clustering using a hierarchical clustering algorithm to achieve the final droplet assignments.

The R computing language is characteristically limited in terms of memory management over other languages like C and parallel platforms like Spark (which can be implemented through Java, Scala, Python or R); thus, while the simulations below use a small number of EVs per sample (on the order of 20 EVs), using the same methods in a programming platform or language such as C or Spark would allow for much larger simulated datasets that mimic close to the reality of about 2×E12 EVs per 1 mL of blood serum sample. In fact, the 'igraph' package itself is available in both C and python implementation versions. The R package version was implemented for ease of use and rapid prototyping to evaluate what parameters are most important in effecting end accuracy of the sequencing methods. Thus, the exact range of parameter values presented here is only exemplary and does not cover all possible parameter values, in particular for real-life data. The results, as shown here, do not significantly change with a larger scale of data. The more important parameter is simply the amount of noise added to the sequencing data.

Simulation Results

Figure 6:
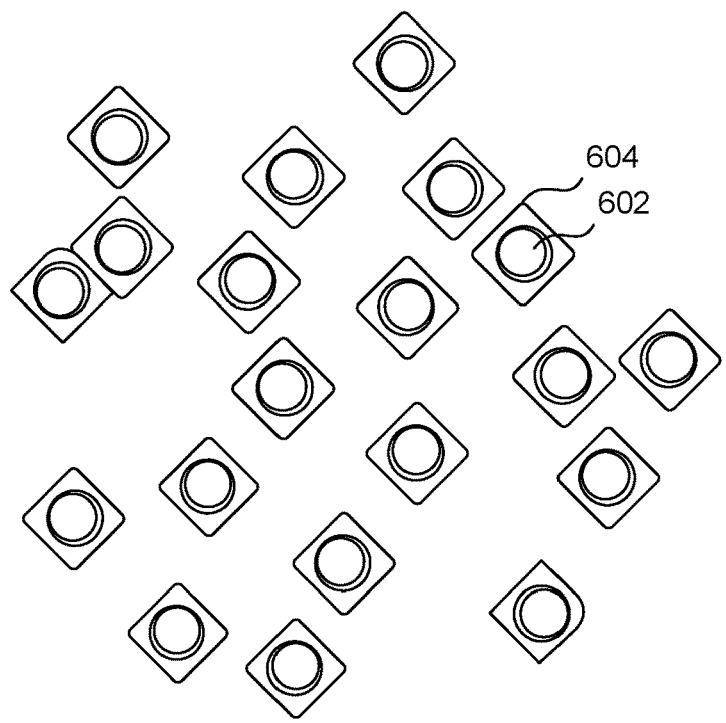
FIG. 6 Illustrates an example of the output from the computational algorithm portions of the present disclosure that virtually demultiplexes UMI-UMI pairs into individual droplet (EV) assignments, assuming zero sequencing errors in the data.
Figure 7:
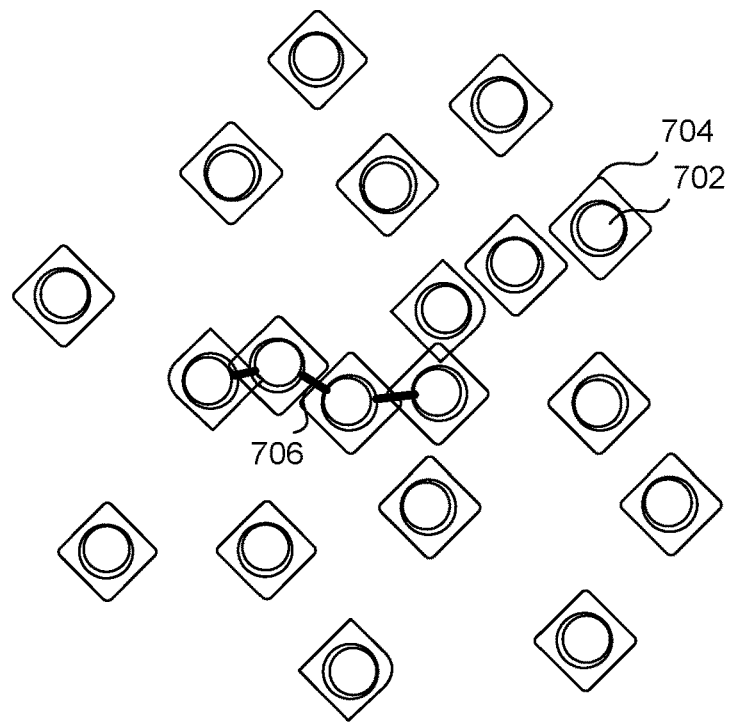
FIG. 7 Illustrates an example of the output from the computational algorithm portions of the present disclosure that virtually demultiplexes UMI-UMI pairs into individual droplet (EV) assignments, assuming approximately 5% sequencing error/noise in the data.

Table 2 reports the simulation results, ordered by lowest error rate to highest error rate. "E" denotes the edge betweenness method and "W" denotes the Walktrap method; both methods performed well under increasing levels of noise. "I" denotes an input parameter (such as error that was purposefully inputted during the simulation) and the final column is denoted "O" for output, which is the percentage of UMIs that were assigned to incorrect droplets. Thus, a zero in this final column means 100% accurate demultiplexing. The results illustrate that one of the most important parameters in lowering error rate (the final column in the table) is the amplification rate; in certain cases with zero noise, an amplification rate of 2 still results in high droplet assignment error rates. Above an amplification rate of 2, simulated added noise must be significantly higher than the standard sequencing error rate of approximately 0.1% to cause a UMI to be assigned to the incorrect droplet. Here, the UMI is defined as all UMI replicates created as a result of amplifying the UMI during the standard sequencing process before running this virtual demultiplexing step. These simulations show that a computational-based deconvolution algorithm can successfully identify which UMIs, and thus which antibodies, and RNA, was originally present in each individual EV. FIG. 6 displays one such example using zero noise, 20 EVs, 0.15 RNAs per EV and 15 antibodies per EV as input parameters. The nodes are UMIs and are tightly clustered over other UMIs in the same droplet; each UMI is one unique circle 602 in FIG. 6. The diamond-shaped outline 604 around each crowded cluster of UMIs (circles) is the algorithm's droplet assignment. Any variability in the shapes of the diamonds should not be interpreted as any unique characteristic attributed to a certain diamond/EV, but simply the output of the automated plotting program translated from the figure directly plotted using the R programming language to accommodate all diamond shapes/droplets on the same figure. Each set of circles assigned to a droplet is so distinctly clustered that the edges between the circles cannot be directly visualized; this is because often each droplet contains several UMIs/circles clustered together. Multiple UMIs are closely connected via edges and thus must be layered on top of each other to produce a 2-dimensional representation of this network of UMI-droplet assignments. Because all nodes are encapsulated within their droplet assignment, FIG. 6 displays a scenario with 100% correct assignment of UMIs to droplets. This means that no UMIs/circles were assigned to the wrong droplet; given this visualization is a result of a simulation, we have the original true droplet assignments for each UMI to confirm the accuracy of the assignments visualized. The shapes in FIG. 7, such as the circles and the diamond shapes, represent the same concepts as in FIG. 6. Thus, circles 702 represent UMIs, which are clustered into droplet assignments, which are the diamond shapes 704. Multiple UMIs are closely connected via edges and thus must be layered on top of each other to produce a 2-dimensional representation of this network of UMI-droplet assignments. FIG. 7, like FIG. 6, also displays 100% accuracy using the same simulation settings except that a noise level of 5% was used to create the input data for the network detection algorithm; thus, there are a few spurious or simulated error edges between a few UMIs that are actually derived from different droplets/diamond outlines. These spurious edges 706 are bolded for ease of visualization, but this enhanced boldness is not directly corrected to the weight of these edges (the actual weight of edges between UMIs in FIGS. 6 and 7 represents how many replicates between two UMIs co-occurred as a single read that was then sequenced.) In FIG. 7, despite these spurious edges, all UMIs/circles were still assigned to their correct original droplet of origin; this is because, these few spurious edges did not represent enough frequency of UMI amplified replicates to cause the algorithm to assign any UMIs to an incorrect droplet. Given this visualization is a result of a simulation, we have the original true droplet assignments for each UMI to confirm the accuracy of the assignments visualized. The algorithm used for FIGS. 6 and 7 was the Edge Betweenness algorithm.

Figure 8:
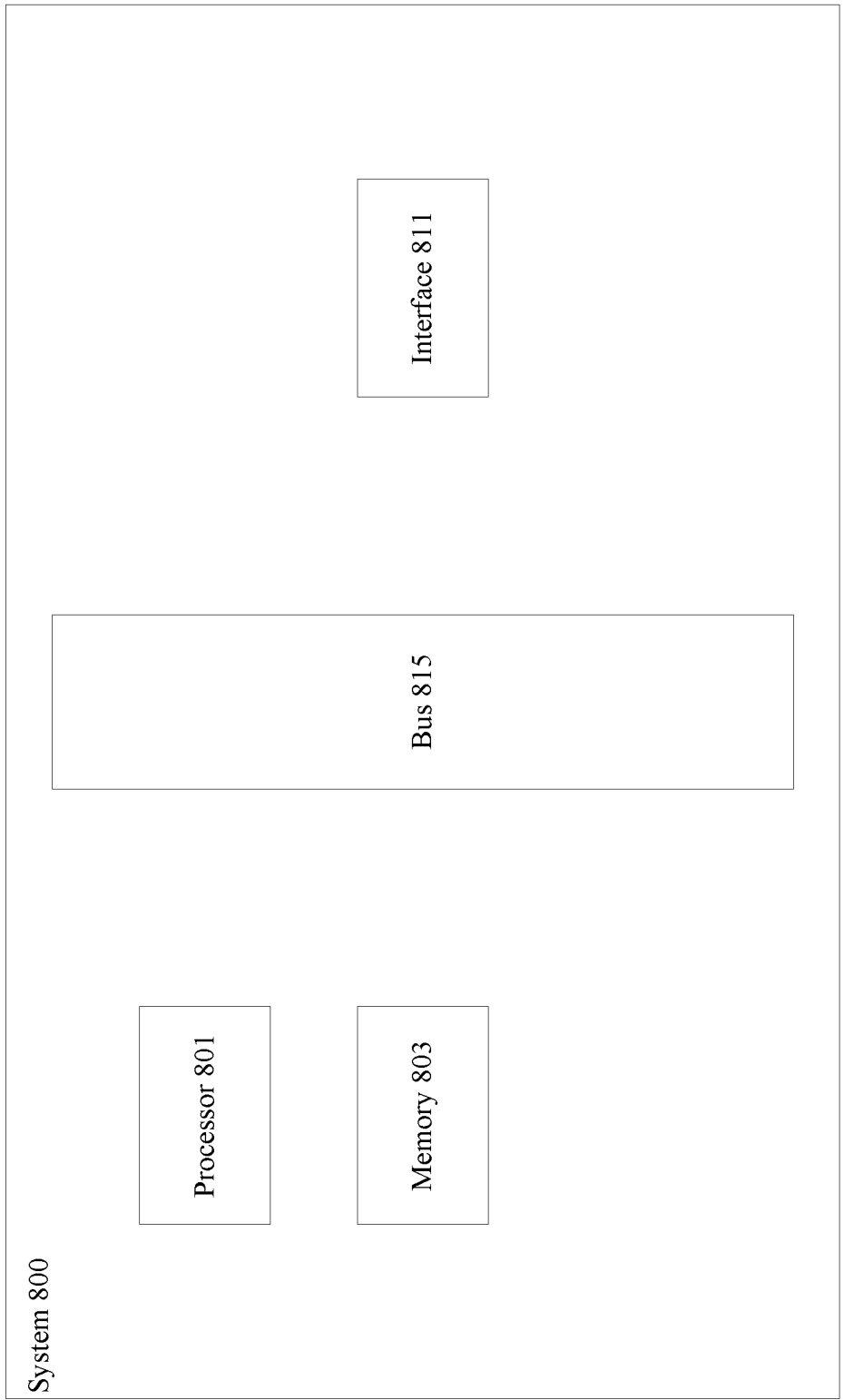
FIG. 8 illustrates an example system for computing algorithms and performing various steps of the methods disclosed herein, in accordance with embodiments of the present disclosure.

FIG. 8 illustrates one example of a system 800 for computing algorithms and performing various steps of the methods described herein, in accordance with one or more embodiments. According to particular embodiments, a system 800, suitable for implementing particular embodiments of the present disclosure, includes a processor 801, a memory 803, an interface 811, and a bus 815 (e.g., a PCI bus or other interconnection fabric) and can operate as a streaming server. In some embodiments, when acting under the control of appropriate software or firmware, the processor 801 is responsible for processing inputs through various computational layers and algorithms. In other embodiments, the processor is responsible for simulating sequences as described above. Various specially configured devices can also be used in place of a processor 801 or in addition to processor 801. The interface 811 is typically configured to send and receive data packets or data segments over a network.

Particular examples of interfaces supports include Ethernet interfaces, frame relay interfaces, cable interfaces, DSL interfaces, token ring interfaces, and the like. In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the system 800 uses memory 803 to store data and program instructions for computing algorithms and running simulations. The program instructions may control the operation of an operating system and/or one or more applications, for example. The memory or memories may also be configured to store received metadata and batch requested metadata.

Because such information and program instructions may be employed to implement the systems/methods described herein, the present disclosure relates to tangible, or non-transitory, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

Accordingly, the preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A method for characterizing protein and nucleic acid content of individual particles, the method comprising:
    encapsulating a plurality of particles into compartments, the compartments also containing analyte specific binding complements with oligonucleotide tags, the tags including a sequence to identify the analyte specific binding complement and two unique molecular identifier (UMI) sequences separated by a restriction enzyme cleavage site;
    amplifying the tags;
    using an enzyme to cut at the restriction site;
    allowing cut tags to re-hybridize;
    pooling the compartments;
    sequencing the oligonucleotide tag sequences; and
    predicting co-encapsulated analytes by computational identification of clusters based on more frequently found UMI pairs.

2. The method of claim 1, wherein the particles are lipid vesicles.

3. The method of claim 2, wherein encapsulating the plurality of particles includes using one or more of the following: polymer-based precipitation methods, size exclusion chromatography, ultrafiltration, ultracentrifugation, flotation density gradient, microfluidic and immunoaffinity methods.

4. The method of claim 1, wherein the oligonucleotide tags include a nucleic acid binding end to bind to nucleic acids associated with the encapsulated individual particle.

5. The method of claim 4, wherein the nucleic acid binding end is a poly-A tail.

6. The method of claim 1, where the compartments are formed by an emulsion.

7. The method of claim 6, wherein encapsulating the plurality of particles includes emulsifying the particles into droplets.

8. The method of claim 7, wherein emulsifying the particles into droplets is achieved using a droplet generator, a home-made microfluidic droplet generating device, or through vigorous shaking.

9. The method of claim 1, wherein the compartments are formed by microfabricated microwells to allow for easier subsequent processing.

10. The method of claim 1, further comprising lysing of the particles if intravesicular nucleotides or analytes need to be accessed.

11. The method of claim 10, wherein lysing vesicles includes injecting a new line of buffer containing exosome lysis reagents into each droplet.

12. The method of claim 10 where lysing of vesicles includes a freeze thaw cycle.

13. The method of claim 1, further comprising a cleanup step and purifying step during sequencing.

14. The method of claim 1, wherein the oligonucleotide tags are freed from their analyte specific binding complements includes using light to cleave a photocleavable linker.

15. The method of claim 1, wherein nucleic acids associated with the encapsulated individual particle bind to the oligonucleotide tags and are amplified in subsequent processing steps.

16. The method of claim 1, wherein amplifying the tags includes using overlap extension polymerase chain reaction.

17. The method of claim 1, further comprising deactivating the enzyme with heat thereby allowing re-ligating or re-hybridization of singlets to form pairs within the same compartment.

18. The method of claim 1, wherein pooling is achieved by breaking an emulsion.

19. The method of claim 18, wherein breaking of the emulsion includes using demulsifiers, or using electrostatic pulses.

20. The method of claim 1, wherein an oligonucleotide tag contains a homology domain sequence and separate oligonucleotide tags are allowed to hybridize on the homology domain to form a UMI pair.

* * * * *